US012115165B2

(12) United States Patent
Tabuteau

(10) Patent No.: US 12,115,165 B2
(45) Date of Patent: *Oct. 15, 2024

(54) USE OF REBOXETINE TO TREAT NARCOLEPSY

(71) Applicant: AXSOME THERAPEUTICS, INC., New York, NY (US)

(72) Inventor: Herriot Tabuteau, New York, NY (US)

(73) Assignee: Axsome Therapeutics, Inc., New York, NY (US)

( * ) Notice: Subject to any disclaimer, the term of this patent is extended or adjusted under 35 U.S.C. 154(b) by 95 days.

This patent is subject to a terminal disclaimer.

(21) Appl. No.: 17/845,767

(22) Filed: Jun. 21, 2022

(65) Prior Publication Data

US 2022/0362252 A1 Nov. 17, 2022

Related U.S. Application Data

(60) Continuation of application No. 17/398,368, filed on Aug. 10, 2021, now Pat. No. 11,364,245, which is a continuation of application No. 17/177,554, filed on Feb. 17, 2021, now Pat. No. 11,135,226, which is a division of application No. 17/119,792, filed on Dec. 11, 2020, now Pat. No. 11,020,402, which is a continuation-in-part of application No. PCT/US2020/062560, filed on Nov. 30, 2020, which is a continuation-in-part of application No. 16/740,410, filed on Jan. 11, 2020, now abandoned, said application No. 17/119,792 is a continuation-in-part of application No. 16/740,409, filed on Jan. 11, 2020, now Pat. No. 11,351,175, said application No. PCT/US2020/062560 is a continuation-in-part of application No. 16/740,411, filed on Jan. 11, 2020, and a continuation-in-part of application No. 16/740,409, filed on Jan. 11, 2020, now Pat. No. 11,351,175, and a continuation-in-part of application No. 16/740,329, filed on Jan. 10, 2020, now abandoned, said application No. 16/740,409 is a continuation-in-part of application No. PCT/US2019/056134, filed on Oct. 14, 2019.

(60) Provisional application No. 62/946,295, filed on Dec. 10, 2019, provisional application No. 62/943,077, filed on Dec. 3, 2019, provisional application No. 62/745,956, filed on Oct. 15, 2018.

(51) Int. Cl.
*A61K 31/5375* (2006.01)
*A61P 25/20* (2006.01)

(52) U.S. Cl.
CPC .......... *A61K 31/5375* (2013.01); *A61P 25/20* (2018.01)

(58) Field of Classification Search
CPC ................................................ A61K 31/5375
See application file for complete search history.

(56) References Cited

U.S. PATENT DOCUMENTS

| | | |
|---|---|---|
| 6,228,398 B1 | 5/2001 | Devane et al. |
| 6,395,788 B1 | 5/2002 | Inglehart |
| 6,441,038 B1 | 8/2002 | Loder et al. |
| 6,465,458 B1 | 10/2002 | Wong et al. |
| 6,485,746 B1 | 11/2002 | Campbell et al. |
| 6,610,690 B2 | 8/2003 | Wong et al. |
| 6,622,036 B1 | 9/2003 | Suffin |
| 6,632,451 B2 | 10/2003 | Penhasi et al. |
| 6,642,235 B2 | 11/2003 | Wong et al. |
| 6,703,389 B2 | 3/2004 | Wong et al. |
| 6,987,107 B2 | 1/2006 | Wong et al. |
| 7,241,762 B2 | 7/2007 | Wong et al. |
| 7,276,503 B2 | 10/2007 | Wong et al. |
| 7,317,011 B2 | 1/2008 | Wong et al. |
| 7,338,953 B2 | 3/2008 | Wong et al. |
| 7,723,334 B2 | 5/2010 | Wong et al. |
| 8,512,751 B2 | 8/2013 | Rariy et al. |
| 8,562,951 B2 | 10/2013 | Suffin et al. |
| 9,034,874 B2 | 5/2015 | Auberson et al. |
| 9,211,293 B2 | 12/2015 | Deaver et al. |
| 9,216,182 B2 | 12/2015 | Wang et al. |
| 9,359,290 B2 | 6/2016 | Khayrallah et al. |
| 9,624,192 B2 | 4/2017 | Auberson et al. |
| 9,750,734 B2 | 9/2017 | Mouthon et al. |
| 9,763,884 B2 | 9/2017 | Bloemers et al. |
| 11,020,402 B2 | 6/2021 | Tabuteau |
| 11,135,226 B2 | 10/2021 | Tabuteau |

(Continued)

FOREIGN PATENT DOCUMENTS

| | | |
|---|---|---|
| CL | 200001765 | 7/2001 |
| CL | 200802868 | 1/2009 |

(Continued)

OTHER PUBLICATIONS

U.S. Appl. No. 17/845,767, filed Jun. 21, 2022 First Named Inventor: Herriot Tabuteau Assignee: Axsome Therapeutics, Inc.
Tabuteau, International Preliminary Report on Patentability, PCT/US2020/062560, mailed Jun. 16, 2022.
U.S. Appl. No. 17/536,669, filed Nov. 29, 2021 First Named Inventor: Herriot Tabuteau Assignee: Axsome Therapeutics, Inc.
U.S. Appl. No. 17/751,490, filed May 23, 2022 First Named Inventor: Herriot Tabuteau Assignee: Axsome Therapeutics, Inc.
Larrosa, O. et al., Stimulant and Anticataplectic Effects of Reboxetine in Patients with Narcolepsy: A Pilot Study, Sleep, 24(3), 282-285, May 2001.

(Continued)

*Primary Examiner* — Nizal S Chandrakumar
(74) *Attorney, Agent, or Firm* — Procopio, Cory, Hargreaves & Savitch LLP

(57) ABSTRACT

Described herein are methods of treating narcolepsy with cataplexy, comprising administering reboxetine (including esreboxetine) to a human being in need thereof. Reboxetine (including esreboxetine) may also be used in the manufacture of a medicament for the treatment of narcolepsy with cataplexy. Also disclosed herein are kits comprising a pharmaceutical composition comprising reboxetine (including esreboxetine) and instructions to use the pharmaceutical composition to treat narcolepsy with cataplexy in a human being.

14 Claims, 5 Drawing Sheets

(56) References Cited

U.S. PATENT DOCUMENTS

| | | |
|---|---|---|
| 11,185,547 B2 | 11/2021 | Tabuteau |
| 11,351,175 B2 | 6/2022 | Tabuteau |
| 11,364,245 B2 | 6/2022 | Tabuteau |
| 11,883,408 B2 | 1/2024 | Tabuteau |
| 2003/0040464 A1 | 2/2003 | Wong et al. |
| 2006/0039890 A1 | 2/2006 | Renshaw et al. |
| 2008/0020039 A1 | 1/2008 | Parikh et al. |
| 2008/0103145 A1 | 5/2008 | Wong et al. |
| 2008/0261984 A1 | 10/2008 | Hughes et al. |
| 2009/0023705 A1 | 1/2009 | Roberts et al. |
| 2009/0275562 A1 | 11/2009 | Rao et al. |
| 2011/0052648 A1 | 3/2011 | Avramoff et al. |
| 2012/0035121 A1 | 2/2012 | Rudnic et al. |
| 2013/0017262 A1 | 1/2013 | Mullen et al. |
| 2014/0275244 A1 | 9/2014 | Khayrallah et al. |
| 2016/0244426 A1 | 8/2016 | Auberson et al. |
| 2019/0381056 A1 | 12/2019 | Tabuteau |
| 2020/0147093 A1 | 5/2020 | Tabuteau |
| 2020/0147094 A1 | 5/2020 | Tabuteau |
| 2020/0147095 A1 | 5/2020 | Tabuteau |
| 2020/0147096 A1 | 5/2020 | Tabuteau |
| 2021/0015823 A1 | 1/2021 | Tabuteau |
| 2021/0100808 A1 | 4/2021 | Tabuteau |
| 2021/0100809 A1 | 4/2021 | Tabuteau |
| 2021/0169893 A1 | 6/2021 | Tabuteau |
| 2021/0252007 A1 | 8/2021 | Tabuteau |
| 2021/0369722 A1 | 12/2021 | Tabuteau |
| 2022/0249501 A1 | 8/2022 | Tabuteau |
| 2022/0280524 A1 | 9/2022 | Tabuteau |
| 2022/0313699 A1 | 10/2022 | Tabuteau |
| 2022/0362252 A1 | 11/2022 | Tabuteau |

FOREIGN PATENT DOCUMENTS

| | | |
|---|---|---|
| EP | 1632235 A2 | 3/2006 |
| EP | 1536791 B1 | 1/2010 |
| EP | 2514417 A2 | 10/2012 |
| WO | 1995028148 A1 | 10/1995 |
| WO | 0039072 | 7/2000 |
| WO | 0101973 A2 | 1/2001 |
| WO | 0147503 A1 | 7/2001 |
| WO | 0162236 A2 | 8/2001 |
| WO | 2006069030 A1 | 6/2006 |
| WO | 2008137923 A2 | 11/2008 |
| WO | 2009049215 A1 | 4/2009 |
| WO | 2009062318 | 5/2009 |
| WO | 2011107749 A2 | 9/2011 |
| WO | 2011107750 A2 | 9/2011 |
| WO | 2011107755 A2 | 9/2011 |
| WO | 2018200775 A1 | 11/2018 |
| WO | 2019245975 A1 | 12/2019 |
| WO | 2020081461 A1 | 4/2020 |

OTHER PUBLICATIONS

Summary of Product Characteristics, EDRONAX (reboxetine), last updated on UK electronic Medicines Compendium (eMC), Oct. 23, 2015.
Hajos, M. et al., The Selective Norepinephrine Reuptake Inhibitor Antidepressant Reboxetine: Pharmacological and Clinical Profile, CNS Drug Reviews, 10(1), 23-44, Mar. 2004.
Schmidt, C. et al., The norepinephrine reuptake inhibitor reboxetine is more potent in treating murine narcoleptic episodes than the serotonin reuptake inhibitor escitalopram, Behavioural Brain Research, 308, 205-210, Jul. 2016.
Sepede, G. et al., Reboxetine in clinical practice: a review, Clin Ter., 163(4), e255-e262, Jul. 2012.
U.S. National Library of Medicine, ClinicalTrials.gov Identifier NCT03881852, Clinical Outcomes in Narcolepsy and Cataplexy: An Evaluation of Reboxetine Treatment (CONCERT), 2019; downloaded from: https://clinicaltrials.gov/ct2/show/NCT03881852 on Jul. 17, 2019.
Aloe, F. et al., Brazilian guidelines for the treatment of narcolepsy, Brazilian Journal of Psychiatry, 32(3), 305-314, Sep. 2010.
Doksat et al., A Case of Profound Weight Loss Secondary to use of Reboxetine, J Child Adolesc Behav 2014, 2:3, 2014.
Shands, Drugs & Therapy Bulletin, vol. 21, No. 10, 2007.
Preetha et al., Biphasic Drug Delivery in Controlled Release Formulations—A Review. IJ PT, 6(4), 3046-3060, Apr. 2015.
Edronax, Package Leaflet: Information for the User, 2020.
Sankar et al., What is a missed dose? Implications for construct validity and patient adherence, AIDS Care, 19(6), 775-780, Jul. 2007.
Tabuteau, International Search Report and Written Opinion, PCT/US 2019/056134, mailed Jan. 30, 2020.
Daniels et al., Health-related quality of life in narcolepsy, J. Sleep Res., 10(1), 75-81, Mar. 2001.
Tabuteau, International Search Report and Written Opinion, PCT/US2019/037500, mailed Oct. 31, 2019.
Tabuteau, International Preliminary Report on Patentability, PCT/US2019/037500, mailed Dec. 30, 2020.
Sateia et al., International Classification of Sleep Disorders, Chest, 146(5), 1387-1394, Nov. 2014.
Kallweit et al., Patient-Reported Measures of Narcolepsy: The Need for Better Assessment, Journal of Clinical Sleep Medicine, 13(5), 737-744, 2017.
Tabuteau, International Search Report and Written Opinion, PCT/US2020/062560, mailed Feb. 18, 2021.
Tabuteau, International Preliminary Report On Patentability, PCT/US2019/056134, mailed Apr. 29, 2021.
Thorpy, Recently Approved and Upcoming Treatments for Narcolepsy, CNS Drugs, 34: 9-27, 2020.
Szabo et al., Neurobiological and Immunogenetic Aspects of Narcolepsy: Implications for Pharmacotherapy, Sleep Med Rev. 43: 23-36, Feb. 2019.
Hublin et al., The Ullanlinna Narcolepsy Scale: validation of a measure of symptoms in the narcoleptic syndrome, Journal of Sleep Research, 3(1), 52-59, Mar. 1994.
Ullanlinna Narcolepsy Scale; the printable version accessed online at: healthysleep.med.harvard. edu/narcolepsy/ diagnosing-narcolepsy/ narcolepsy-self-evaluation, content last updated Feb. 2018.
European Extended Search Report and Written Opinion for related application 19874099.5, dated Dec. 7, 2021.
Garcia-Borreguero, D. et al., Effects of Reboxetine in Narcolepsy-Cataplexy: Preliminary findings on 14 patients, Sleep, vol. 24, No. Abstract Supplement, pages A323-A324, Jun. 2001.
O'gorman, C. et al., Scientific Rational and Clinical Development of AXS-12 for Narcolepsy, Sleep, vol. 42, No. Abstract Supplement, page A24, Jan. 2019.
Szakacs, Z. et al., Safety and efficacy of pitolisant on cataplexy in patients with narcolepsy: a randomised, double- blind, placebo-controlled trial, The Lancet Neurology, 16(3), 200-207, Mar. 2017.
Berro, L.F. et al., A journey through narcolepsy diagnosis: From ICSD 1 to ICSD 3, Sleep Science, 7(1), Mar. 2014.
Lehert, P. et al., Comparing symptom measurement tools in pediatric narcolepsy, Sleep Epidemiology, 2:100032, Dec. 2022.

Ability to concentrate was collected daily on a 5-point scale where
1=very good, 2=good, 3=average, 4=poor, 5=very poor

USE OF REBOXETINE TO TREAT NARCOLEPSY

CROSS-REFERENCE TO RELATED APPLICATIONS

This application is a continuation of U.S. patent application Ser. No. 17/398,368, filed Aug. 10, 2021; which is a continuation of Ser. No. 17/177,554, filed Feb. 17, 2021, now U.S. Pat. No. 11,135,226; which is a division of U.S. patent application Ser. No. 17/119,792, filed Dec. 11, 2020, now U.S. Pat. No. 11,020,402; which is a continuation-in-part of International Pat. App. No. PCT/US2020/062560, filed Nov. 30, 2020; which is a continuation-in-part of U.S. patent application Ser. No. 16/740,329, filed Jan. 10, 2020, now abandoned; Ser. No. 16/740,409, filed Jan. 11, 2020, now U.S. Pat. No. 11,351,175; 16/740,410, filed Jan. 11, 2020, now abandoned; and Ser. No. 16/740,411, filed Jan. 11, 2020, now abandoned; International Pat. App. No. PCT/US2020/062560 also claims the benefit of U.S. Prov. Pat. App. Nos. 62/943,077, filed Dec. 3, 2019; and 62/946,295, filed Dec. 10, 2019; U.S. patent application Ser. No. 17/119,792 is also a continuation-in-part of U.S. patent application Ser. No. 16/740,409, filed Jan. 11, 2020, now U.S. Pat. No. 11,351,175; which is a continuation-in-part of International Pat. App. No. PCT/US2019/056134, filed Oct. 14, 2019; which claims the benefit of U.S. Prov. Pat. App. No. 62/745,956, filed Oct. 15, 2018; U.S. patent application Ser. No. 16/740,409 also claims the benefit of U.S. Prov. Pat. App. Nos. 62/943,077, filed Dec. 3, 2019; and 62/946,295, filed Dec. 10, 2019; all of the above applications, U.S. patents issued from, or U.S. publications of any of the above applications are incorporated by reference in their entirety.

BACKGROUND

Narcolepsy is a serious and debilitating neurological condition that causes dysregulation of the sleep-wake cycle and is characterized clinically by excessive daytime sleepiness (EDS), cataplexy, hypnagogic hallucinations, sleep paralysis, and disrupted nocturnal sleep. Narcolepsy is estimated to afflict an estimated 185,000 individuals in the U.S. Cataplexy is seen in an estimated 70% of narcolepsy patients and is a sudden reduction or loss of muscle tone while a patient is awake, typically triggered by strong emotions such as laughter, fear, anger, stress, or excitement. Type 1 narcolepsy includes cataplexy, while Type 2 narcolepsy does not include cataplexy. Narcolepsy interferes with cognitive, psychological, and social functioning, increases the risk of work- and driving-related accidents, and is associated with a 1.5 fold higher mortality rate. Depression is reported in up to 57% of patients. Unfortunately, currently approved treatments are few for this under-diagnosed orphan condition and are limited by variability in efficacy from patient to patient, tolerability issues and the need for Drug Enforcement Administration (DEA) scheduling.

SUMMARY

Described herein are methods of treating a nervous system disorder, comprising administering an antidepressant, such as a selective norepinephrine inhibitor, e.g., atomoxetine, edivoxetine, reboxetine, or S,S-reboxetine to a human being in need thereof.

Described herein are methods of treating narcolepsy with cataplexy, comprising administering an antidepressant, such as a selective norepinephrine inhibitor, e.g., atomoxetine, edivoxetine, or reboxetine (including S,S-reboxetine), to a human being in need thereof.

Some embodiments include use of an antidepressant, such as a selective norepinephrine inhibitor, e.g., atomoxetine, edivoxetine, or reboxetine (including S,S-reboxetine), in the manufacture of a medicament for the treatment of narcolepsy with cataplexy.

Some embodiments include a kit comprising a pharmaceutical composition comprising an antidepressant, such as a selective norepinephrine inhibitor, e.g., atomoxetine, edivoxetine, or reboxetine (including S,S-reboxetine), and instructions to use the pharmaceutical composition to treat narcolepsy with cataplexy in a human being.

In some embodiments, an antidepressant, such as a selective norepinephrine inhibitor, e.g., atomoxetine, edivoxetine, or reboxetine (including S,S-reboxetine), is administered at least once daily for more than two weeks. In some embodiments, the human being experiences a reduction in the number of cataplexy attacks in a week, a reduction in the Epworth Sleepiness Scale (ESS) score, a reduction in the Maintenance of Wakefulness Test (MWT) score, a reduction in the Narcolepsy Symptom Assessment Score (NSAQ), a reduction in the Patient Global Impression of Severity (PGI-S) score, a score below 4 in the Patient Global Impression of Change (PGI-C), or a reduction in the Hamilton Depression Rating Scale (HAM-D), or improvement in the ability to concentrate (e.g. on the NSAQ) as a result of the treatment.

Some embodiments include a method of rapidly reducing the number of cataplexy attacks in a human being having narcolepsy with cataplexy, comprising administering about 8 mg to about 10 mg of reboxetine daily for at least two weeks to a human being in need thereof, wherein one week after the start of the treatment, the human being has at least 30% fewer cataplexy attacks as compared to baseline and the reduction in the number of cataplexy attacks is statistically significant as compared to administering a placebo with $p<0.01$. In some embodiments, the reduction in the number of cataplexy attacks is statistically significant as compared to administering a placebo with $p<0.001$.

Some embodiments include a method of improving the ability to concentrate comprising administering an antidepressant, such as a selective norepinephrine inhibitor, e.g., atomoxetine, edivoxetine, or reboxetine (including S,S-reboxetine), to a mammal or a human being in need thereof.

Some embodiments include a method of improving the ability to concentrate in a human being having narcolepsy with cataplexy, comprising administering about 8 mg to about 10 mg of reboxetine daily for at least two weeks to a human being in need thereof, wherein, prior to the start of treatment, the human being has an ability to concentrate that is "average," "poor," or "very poor," and two weeks after the start of the treatment, the human being has an ability to concentrate that is "good" or "very good," as determined by the Ability to Concentrate Item of the Narcolepsy Symptom Assessment Questionnaire. In some embodiments, the reboxetine is racemic reboxetine. In some embodiments, the reboxetine is esreboxetine.

Some embodiments include a method of reducing the number of inadvertent naps in a human being having narcolepsy with cataplexy, comprising administering about 8 mg to about 10 mg of reboxetine daily for at least two weeks to a human being in need thereof, wherein two weeks after the start of the treatment, the human being has at least 20% fewer inadvertent naps per week as compared to the week before the patient first receives reboxetine. In some embodiments, the reboxetine is racemic reboxetine. In some embodiments, the reboxetine is esreboxetine.

Some embodiments include a method of improving sleep quality in a human being having narcolepsy with cataplexy, comprising administering about 8 mg to about 10 mg of reboxetine daily for at least two weeks to a human being in need thereof, wherein two weeks after the start of the treatment, the human being reports having improved sleep quality as compared to the week before the patient first receives reboxetine. In some embodiments, the reboxetine is racemic reboxetine. In some embodiments, the reboxetine is esreboxetine.

Some embodiments include a method of reducing night awakenings in a human being having narcolepsy with cataplexy, comprising administering about 8 mg to about 10 mg of reboxetine daily for at least two weeks to a human being in need thereof, wherein two weeks after the start of the treatment, the human being reports having fewer night awakenings as compared to the week before the patient first receives reboxetine. In some embodiments, the reboxetine is racemic reboxetine. In some embodiments, the reboxetine is esreboxetine.

Some embodiments include a method of reducing sleep paralysis in a human being having narcolepsy with cataplexy, comprising administering about 8 mg to about 10 mg of reboxetine daily for at least two weeks to a human being in need thereof, wherein two weeks after the start of the treatment, the human being reports having fewer sleep paralysis episodes as compared to the week before the patient first receives reboxetine. In some embodiments, the reboxetine is racemic reboxetine. In some embodiments, the reboxetine is esreboxetine.

Some embodiments include a method of reducing hypnagogic hallucinations in a human being having narcolepsy with cataplexy, comprising administering about 8 mg to about 10 mg of reboxetine daily for at least two weeks to a human being in need thereof, wherein two weeks after the start of the treatment, the human being reports having fewer hypnagogic hallucinations as compared to the week before the patient first receives reboxetine. In some embodiments, the reboxetine is racemic reboxetine. In some embodiments, the reboxetine is esreboxetine.

Some embodiments include a method of improving the ability to concentrate in a human being suffering from narcolepsy, comprising administering reboxetine to a human being in need thereof. In some embodiments, the reboxetine is racemic reboxetine. In some embodiments, the reboxetine is esreboxetine.

Some embodiments include a method of treating narcolepsy with cataplexy, comprising administering reboxetine to a human being in need thereof, wherein reboxetine is administered at least once daily for more than two weeks, wherein, two weeks after the beginning of treatment, the human being experiences a reduction in the number of cataplexy attacks in a week, a reduction in the Epworth Sleepiness Scale score, a decrease in the cataplexy subscore on the Ullanlinna Narcolepsy Scale (NUS), or a reduction in the Maintenance of Wakefulness Test score as a result of the treatment.

Some embodiments include use of reboxetine in the manufacture of a medicament for the treatment of narcolepsy with cataplexy, wherein reboxetine is administered at least once daily for at least three weeks. In some embodiments, the reboxetine is racemic reboxetine. In some embodiments, the reboxetine is esreboxetine.

Some embodiments include a kit comprising a pharmaceutical composition comprising reboxetine and instructions to use the pharmaceutical composition to treat narcolepsy with cataplexy in a human being, wherein reboxetine is administered at least once daily for at least three weeks. In some embodiments, the reboxetine is racemic reboxetine. In some embodiments, the reboxetine is esreboxetine.

Some embodiments include a method of treating fibromyalgia, comprising administering esreboxetine to a human being in need thereof, wherein a daily dose of about 1 mg to about 2 mg of esreboxetine is administered for at least six weeks, wherein the human being experiences a reduction in fibromyalgia pain during the course of the treatment, as measured by a visual analog scale (VAS) score, that is greater than the reduction in pain that the human being would have experienced by administering a placebo.

Some embodiments include a method of treating fibromyalgia, comprising administering esreboxetine to a human being in need thereof, wherein a daily dose of about 2 mg to about 4 mg of esreboxetine is administered for at least six weeks, wherein the human being experiences a reduction in pain during the course of the treatment, as measured by a visual analog scale (VAS) score, that is greater than the reduction in pain that the human being would have experienced by administering a placebo.

Some embodiments include a method of treating fibromyalgia, comprising administering esreboxetine to a human being in need thereof, wherein a daily dose of about 0.5 mg to about 1 mg of esreboxetine is administered for at least six weeks, wherein the human being experiences a reduction in pain during the course of the treatment, as measured by a visual analog scale (VAS) score, that is greater than the reduction in pain that the human being would have experienced by administering a placebo.

DETAILED DESCRIPTION

Figure 1:
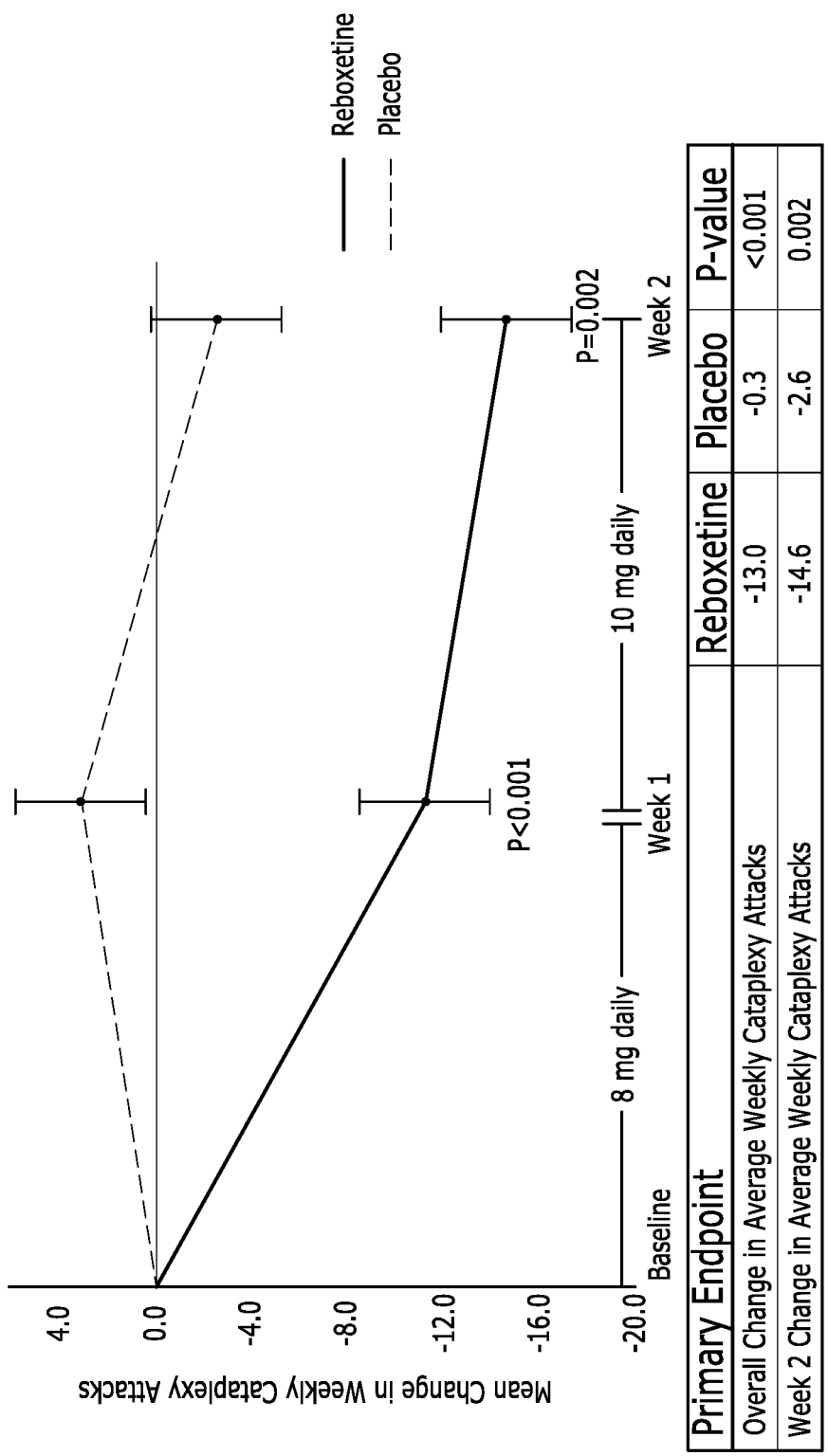
FIG. 1 depicts the change in weekly cataplexy attacks for human patients who received reboxetine or placebo as described in Example 22.

An antidepressant, such as reboxetine or S,S-reboxetine, may be used to treat a condition such as a nervous system disorder, including an addictive disorder (including those due to alcohol, nicotine, and other psychoactive substances), a withdrawal syndrome, an adjustment disorder (including depressed mood, anxiety, mixed anxiety and depressed mood, disturbance of conduct, and mixed disturbance of conduct and mood), depression (including major depressive disorder, alone or in combination with other antidepressants), an age-associated learning or mental disorder (including Alzheimer's disease), anorexia nervosa apathy, an attention-deficit (or another cognitive) disorder due to general medical conditions, attention-deficit hyperactivity disorder (ADHD), bipolar disorder, bulimia nervosa, chronic fatigue syndrome, chronic or acute stress, chronic pain, conduct disorder, cyclothymic disorder, depression (including adolescent depression and minor depression), dysthymic disorder, fibromyalgia and other somatoform disorders (including somatization disorder, conversion disorder, pain disorder, hypochondriasism, body dysmorphic disorder, undifferentiated somatoform disorder, and somatoform NOS), generalized anxiety disorder (GAD), incontinence (i.e., stress incontinence, genuine stress incontinence, and mixed incontinence), stress urinary incontinence, an inhalation disorder, an intoxication disorders (alcohol addiction), mania, migraine headaches, obesity (e.g., reducing the weight of obese or overweight patients), an obsessive compulsive disorder or a related spectrum disorder, oppositional defiant disorder, panic disorder, peripheral neuropathy, post-traumatic stress disorder, premenstrual dysphoric disorder (i.e., premenstrual syndrome and late luteal phase dysphoric disorder), a psychotic disorder (including schizophrenia, negative symptoms of schizophrenia, schizoaffective or schizophreniform disorder, either alone or as an adjuvant therapy), seasonal affective disorder, a sleep disorder (such as narcolepsy or enuresis), social phobia (including social anxiety disorder), a specific developmental disorder, selective serotonin reuptake inhibition (SSRI) "poop out" syndrome (i.e., wherein a patient who fails to maintain a satisfactory response to SSRI therapy after an initial period of satisfactory response), TIC disorders (e.g., Tourette's Disease), post-shingles pain, painful diabetic peripheral neuropathy, postherpetic neuralgia, syncope, and/or vasovagal syncope, etc. In some embodiments, S,S-reboxetine is used to treat fibromyalgia. In some embodiments, reboxetine is used to treat fibromyalgia.

Treatment with reboxetine (including S,S-reboxetine), may result in improvement of the symptoms of a disease. For example, for pain conditions such as fibromyalgia, the patient may experience a reduction in pain measured on a visual analog scale (VAS), such as 0-100 mm, which is greater than what would be experienced by administering a placebo. In some embodiments, the improvement in VAS score be at least about 10%, at least about 20%, at least about 30%, at least about 40%, at least about 50%, at least about 60%, at least about 70%, at least about 80%, at least about 90%, about 1-5%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. at least about 50 mm, at least about 40 mm, at least about 30 mm, at least about 20 mm, at least about 10 mm, about 0-10 mm, about 10-20 mm, about 20-30 mm, about 30-40 mm, about 40-50 mm, about 0-25 mm, or about 25-50 mm more than would be experienced by administering a placebo. In some embodiments, the improvement in VAS score be at least about 10%, at least about 20%, at least about 30%, at least about 40%, at least about 50%, at least about 60%, at least about 70%, at least about 80%, at least about 90%, about 1-5%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. at least about 50 mm, at least about 40 mm, at least about 30 mm, at least about 20 mm, at least about 10 mm, about 0-10 mm, about 10-20 mm, about 20-30 mm, about 30-40 mm, about 40-50 mm, about 0-25 mm, or about 25-50 mm as compared to baseline (e.g. right before treatment starts).

An antidepressant, such as bupropion, hydroxybupropion, erythrohydroxybupropion, threohydroxybupropion, clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, norfluoxetine, dapoxetine, ketamine, etc., including a norepinephrine reuptake inhibitor such as atomoxetine, edivoxetine, or reboxetine (including S,S-reboxetine), have the potential to treat the symptoms of narcolepsy.

Many antidepressants, such as norepinephrine reuptake inhibitors, e.g., atomoxetine, edivoxetine, or reboxetine (including S,S-reboxetine), lack of DEA scheduling, which would represent a significant benefit to patients living with this condition.

A person may have Type 1 narcolepsy if Criteria A and B are met:
  A. The patient has daily periods of irrepressible need to sleep or daytime lapses into sleep occurring for at least 3 months
  B. The presence of one or both of the following:
    1. Cataplexy (as defined under Essential Features) and a mean sleep latency of <8 minutes and Sleep-Onset REM Periods (SOREMPs) on a Mean Sleep Latency Test (MSLT) performed according to standard techniques. A SOREMP (within 15 minutes of sleep onset) on the preceding laboratory-based polysomnography (PSG) may replace one of the SOREMPs on the MSLT
    2. CSF hypocretin-1 concentrations measured by immunoreactivity either <110 pg/mL or <⅓ of mean values obtained in normal subjects with the same assay In young children, narcolepsy may sometimes present as excessively long night sleep or by resumption of previously discontinued daytime napping. If narcolepsy Type 1 is strongly suspected clinically but criteria B2 are not met, a possible strategy is to repeat the MSLT Some patients treated with an antidepressant, including a norepinephrine inhibitor such as reboxetine (including S,S-reboxetine) may have, and/or may be selected for having, daily periods of irrepressible need to sleep or daytime lapses into sleep occurring for at least about 3 months, at least 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 2 years, at least about 3 years, at least about 4 years, at least about 5 years, at least about 10 years, at least about 15 years, at least about 20 years, at least about 25 years, at least about 30 years, at least about 40 years, at least about 50 years, at least about 60 years, about 3-9 months, about 9-18 months, about 18 months to about 2 years, about 2-5 years, about 5-10 years, about 10-15 years, about 15-20 years, about 20-25 years, about 25-30 years, about 30-35 years, about 35-40 years, about 40-50 years, about 50-60 years, or more.

Some patients treated with an antidepressant, including a norepinephrine inhibitor such as reboxetine (including S,S-reboxetine) may have, and/or may be selected for having, a mean sleep latency of less than about 1 minute, less than about 2 minutes, less than about 3 minutes, less than about 4 minutes, less than about 5 minutes, less than about 6 minutes, less than about 7 minutes, less than about 8 minutes, about 0.1-1 minutes, about 1-2 minutes, about 2-3 minutes, about 3-4 minutes, about 4-5 minutes, about 5-6 minutes, about 6-7 minutes, about 7-8 minutes, about 1 minute, about 2 minutes, about 3 minutes, about 4 minutes, about 5 minutes, about 6 minutes, about 7 minutes, or about 8 minutes.

Some patients treated with an antidepressant, including a norepinephrine inhibitor such as reboxetine (including S,S-reboxetine) may have, and/or may be selected for having, at least 2, at least 3, or at least 4 SOREMPs on an MSLT (Mean Sleep Latency Test) performed according to standard techniques. A SOREMP within 15 minutes of sleep onset on the preceding nocturnal PSG may replace one of the SOREMPs on the MSLT Some patients treated with an antidepressant, including a norepinephrine inhibitor such as reboxetine (including S,S-reboxetine) may have, and/or may be selected for having, CSF hypocretin-1 concentrations measured by immunoreactivity that are less than about 40 pg/mL, less than about 50 pg/mL, less than about 60 pg/mL, less than about 70 pg/mL, less than about 80 pg/mL, less than about 90 pg/mL, less than about 100 pg/mL, less than about 110 pg/mL.

Some patients treated with an antidepressant, including a norepinephrine inhibitor such as reboxetine (including S,S-reboxetine) may have, and/or may be selected for having, CSF hypocretin-1 concentrations measured by immunoreactivity that are less than about 1/10, less than about 1/9, less than about 1/8, less than about 1/7, less than about 1/6, less than about 1/5, less than about 1/4, or less than about 1/3 of mean values obtained in normal subjects with the same assay.

Some patients treated with an antidepressant, including a norepinephrine inhibitor such as reboxetine (including S,S-reboxetine) may be, and/or may be selected for being, young children presenting with excessively long night sleep.

Some patients treated with an antidepressant, including a norepinephrine inhibitor such as reboxetine (including S,S-reboxetine) may be, and/or may be selected for being, young children presenting with resumption of previously discontinued daytime napping.

Some patients treated with an antidepressant, including a norepinephrine inhibitor such as reboxetine (including S,S-reboxetine) may have, and/or may be selected for having, a diagnosis of narcolepsy with cataplexy that meets the International Classification of Sleep Disorders, Third Edition (ICSD-3) criteria.

Some patients treated with an antidepressant, including a norepinephrine inhibitor such as reboxetine (including S,S-reboxetine) may have, and/or may be selected for having, a cataplexy subscore on the Ullanlinna Narcolepsy Score (UNS) that is at least 1, at least about 2, at least about 3, at least about 4, at least about 5, at least about 6, at least about 7, at least about 8, at least about 9, at least about 10, about 11, about 1-2, about 2-3, about 3-4, about 4-5, about 5-6, about 6-7, about 7-8, about 8-9, about 9-10, about 10-11, about 2-4, about 4-6, about 6-8, about 8-10, about 2-6, or about 6-10, or any number between 1 and 11.

Some patients treated with an antidepressant, including a norepinephrine inhibitor such as reboxetine (including S,S-reboxetine) may have, and/or may be selected for having, a score on the Epworth Sleepiness Scale (ESS) that is at least about 10, greater than about 10, at least about 11, at least about 12, at least about 13, at least about 14, at least about 15, at least about 16, at least about 17, at least about 18, at least about 19, at least about 20, at least about 21, at least about 22, at least about 23, at least about 24, about 10-11, about 11-12, about 12-13, about 13-14, about 14-15, about 15-16, about 16-17, about 17-18, about 18-19, about 19-20, about 20-21, about 21-22, about 22-23, about 23-24, about 10-13, about 13-16, about 16-19, about 19-22, or about 22-24.

Some patients treated with an antidepressant, including a norepinephrine inhibitor such as reboxetine (including S,S-reboxetine) may have, and/or may be selected for having, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 28, at least about 35, about 7-14, about 14-21, about 21-28, about 28-35, about 35-49, or about 49-70 cataplexy attacks per week.

Some patients treated with an antidepressant, including a norepinephrine inhibitor such as reboxetine (including S,S-reboxetine) may have, and/or may be selected for having, a Maintenance of Wakefulness Test (MWT) score that is less than about 1 minutes, less than about 2 minutes, less than about 3 minutes, less than about 4 minutes, less than about 5 minutes, less than about 6 minutes, less than about 7 minutes, less than about 8 minutes, less than about 9 minutes, less than about 10 minutes, less than about 11 minutes, less than about 12 minutes, less than about 13 minutes, less than about 14 minutes, less than about 15 minutes, less than about 16 minutes, less than about 17 minutes, less than about 18 minutes, less than about 19 minutes, less than about 20 minutes, about 0-1 minutes, about 1-2 minutes, about 2-3 minutes, about 3-4 minutes, about 4-5 minutes, about 5-6 minutes, about 6-7 minutes, about 7-8 minutes, about 8-9 minutes, about 9-10 minutes, about 10-11 minutes, about 11-12 minutes, about 12-13 minutes, about 13-14 minutes, about 14-15 minutes, about 15-16 minutes, about 16-17 minutes, about 17-18 minutes, about 18-19 minutes, about 19-20 minutes, about 0-4 minutes, about 4-8 minutes, about 8-12 minutes, about 12-16 minutes, about 16-20, or about 0-19 minutes.

In some embodiments, the patient has had, and/or may be selected for having had, symptoms of narcolepsy for about 1-5 years, about 5-10 years, about 10-15 years, about 15-20 years, about 20-25 years, about 25-30 years, about 30-35 years, about 35-40 years, about 40-45 years, about 45-50 years, about 50-55 years, about 55-60 years, about 60-65 years, about 65-70 years, about 70-75 years, or more than 75 years prior to receiving an antidepressant, including a norepinephrine inhibitor such as reboxetine (including S,S-reboxetine) for treatment.

In some embodiments, the patient has, and/or may be selected for having, an age of about 0-18 years, about 18-100 years, about 0-5 years, about 5-10 years, about 10-15 years, about 15-18 years, about 18-20 years, about 15-20 years, about 18-25 years, about 20-25 years, about 25-30 years, about 30-35 years, about 35-40 years, about 40-45 years, about 45-50 years, about 50-55 years, about 55-60 years, about 60-65 years, about 65-70 years, about 70-75, or more than 75 years prior to receiving an antidepressant, including a norepinephrine inhibitor such as reboxetine (including S,S-reboxetine) for treatment.

Some patients treated with an antidepressant, including a norepinephrine inhibitor such as reboxetine (including S,S-reboxetine) for narcolepsy (e.g., with cataplexy and/or EDS) may be, and/or may be selected for being female. In some embodiments, the patient may be selected for being female, nonlactating and nonpregnant.

Some patients treated with an antidepressant, including a norepinephrine inhibitor such as reboxetine (including S,S-reboxetine) for narcolepsy (e.g., with cataplexy and/or EDS) may be, and/or may be selected for being male.

Some patients treated with an antidepressant, including a norepinephrine inhibitor such as reboxetine (including S,S-reboxetine) for narcolepsy (e.g., with cataplexy and/or EDS) may not have, and/or may be selected for not having, any concomitant sleep disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, any concomitant sleep disorder other than mild sleep apnea (<15 events per hour) or mild to moderate sleep apnea (<30 events per hour) with stable treatment. Some patients treated with an antidepressant, including a norepinephrine inhibitor such as reboxetine (including S,S-reboxetine) for narcolepsy (e.g., with cataplexy and/or EDS) may not have, and/or may be selected for not having, any clinically significant conditions potentially causing EDS. Some patients treated with an antidepressant, including a norepinephrine inhibitor such as reboxetine (including S,S-reboxetine) for narcolepsy (e.g., with cataplexy and/or EDS) may not have, and/or may be selected for not having, any clinically significant psychiatric disorders. Some patients treated with an antidepressant, including a norepinephrine inhibitor such as reboxetine (including S,S-reboxetine) for narcolepsy (e.g., with cataplexy and/or EDS) may not have, and/or may be selected for not having, any type of depression that was not caused by narcolepsy. Some patients treated with an antidepressant, including a norepinephrine inhibitor such as reboxetine (including S,S-reboxetine) for narcolepsy (e.g., with cataplexy and/or EDS) may not have, and/or may be selected for not having, any sleepiness caused by depression that was not caused by narcolepsy. Some patients treated with an antidepressant, including a norepinephrine inhibitor such as reboxetine (including S,S-reboxetine) for narcolepsy (e.g., with cataplexy and/or EDS) may not have, and/or may be selected for not having, an affective disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a psychiatric disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a cerebral function disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a movement disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a dementia. Some patients treated with an antidepressant, including a norepinephrine inhibitor such as reboxetine (including S,S-reboxetine) for narcolepsy (e.g., with cataplexy and/or EDS) may not have, and/or may be selected for not having, a motor neuron disease.

Some patients treated with an antidepressant, including a norepinephrine inhibitor such as reboxetine (including S,S-reboxetine) for narcolepsy (e.g., with cataplexy and/or EDS) may not be concurrently taking sodium oxybate. Some patients treated with an antidepressant, including a norepinephrine inhibitor such as reboxetine (including S,S-reboxetine) for narcolepsy (e.g., with cataplexy and/or EDS) may not be concurrently taking a stimulant. Some patients treated with an antidepressant, including a norepinephrine inhibitor such as reboxetine (including S,S-reboxetine) for narcolepsy (e.g., with cataplexy and/or EDS) may not be concurrently taking an anticonvulsant. Some patients treated with an antidepressant, including a norepinephrine inhibitor such as reboxetine (including S,S-reboxetine) for narcolepsy (e.g., with cataplexy and/or EDS) may not be concurrently taking clonidine. Some patients treated with an antidepressant, including a norepinephrine inhibitor such as reboxetine (including S,S-reboxetine) for narcolepsy (e.g., with cataplexy and/or EDS) may not be concurrently taking a selective serotonin reuptake inhibitor (SSRI). Some patients treated with an antidepressant, including a norepinephrine inhibitor such as reboxetine (including S,S-reboxetine) for narcolepsy (e.g., with cataplexy and/or EDS) may not be concurrently taking a serotonin and norepinephrine re-uptake inhibitor (SNRI). Some patients treated with an antidepressant, including a norepinephrine inhibitor such as reboxetine (including S,S-reboxetine) for narcolepsy (e.g., with cataplexy and/or EDS) may not be concurrently taking a monoamine oxidase inhibitor (MAOI). Some patients treated with an antidepressant, including a norepinephrine inhibitor such as reboxetine (including S,S-reboxetine) for narcolepsy (e.g., with cataplexy and/or EDS) may not be concurrently taking a tricyclic antidepressant (TCA). Some patients treated with an antidepressant, including a norepinephrine inhibitor such as reboxetine (including S,S-reboxetine) for narcolepsy (e.g., with cataplexy and/or EDS) may not be concurrently taking a hypnotic. Some patients treated with an antidepressant, including a norepinephrine inhibitor such as reboxetine (including S,S-reboxetine) for narcolepsy (e.g., with cataplexy and/or EDS) may not be concurrently taking an anxiolytic. Some patients treated with an antidepressant, including a norepinephrine inhibitor such as reboxetine (including S,S-reboxetine) for narcolepsy (e.g., with cataplexy and/or EDS) may not be concurrently taking a sedating antihistamine. Some patients treated with an antidepressant, including a norepinephrine inhibitor such as reboxetine (including S,S-reboxetine) for narcolepsy (e.g., with cataplexy and/or EDS) may not be concurrently taking an antipsychotic. Some patients treated with an antidepressant, including a norepinephrine inhibitor such as reboxetine (including S,S-reboxetine) for narcolepsy (e.g., with cataplexy and/or EDS) may not be concurrently taking any other medication for the treatment of narcolepsy or cataplexy.

Some patients treated with an antidepressant, including a norepinephrine inhibitor such as reboxetine (including S,S-reboxetine) for narcolepsy (e.g., with cataplexy and/or EDS) may not have, and/or may be selected for not having, a neurodegenerative disease. Some patients treated with an antidepressant, including a norepinephrine inhibitor such as reboxetine (including S,S-reboxetine) for narcolepsy (e.g., with cataplexy and/or EDS) may not have, and/or may be selected for not having, a seizure disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a convulsive disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a diagnosis of cancer (except possibly basal cell carcinoma) within the last 5 years.

Some patients treated with an antidepressant, including a norepinephrine inhibitor such as reboxetine (including S,S-reboxetine) for narcolepsy (e.g., with cataplexy and/or EDS) may not have, and/or may be selected for not having, a bilirubin level more than 2 times the upper limit of normal. Some patients treated with an antidepressant, including a norepinephrine inhibitor such as reboxetine (including S,S-reboxetine) for narcolepsy (e.g., with cataplexy and/or EDS) may not have, and/or may be selected for not having, an alanine aminotransferase level more than 2 times the upper limit of normal. Some patients treated with an antidepressant, including a norepinephrine inhibitor such as reboxetine (including S,S-reboxetine) for narcolepsy (e.g., with cataplexy and/or EDS) may not have, and/or may be selected for not having, an aspartate aminotransferase level more than 2 times the upper limit of normal. Some patients treated with an antidepressant, including a norepinephrine inhibitor such as reboxetine (including S,S-reboxetine) for narcolepsy (e.g., with cataplexy and/or EDS) may not have, and/or may be selected for not having, an alkaline phosphatase level more than 2 times the upper limit of normal.

Some patients treated with an antidepressant, including a norepinephrine inhibitor such as reboxetine (including S,S-reboxetine) for narcolepsy (e.g., with cataplexy and/or EDS) may not have, and/or may be selected for not having clinically significant hypertension. Some patients treated with an antidepressant, including a norepinephrine inhibitor such as reboxetine (including S,S-reboxetine) for narcolepsy (e.g., with cataplexy and/or EDS) may not have, and/or may be selected for not having uncontrolled hypertension. Some patients treated with an antidepressant, including a norepinephrine inhibitor such as reboxetine (including S,S-reboxetine) for narcolepsy (e.g., with cataplexy and/or EDS) may not have, and/or may be selected for not having a history of cardiovascular disease. Some patients treated with an antidepressant, including a norepinephrine inhibitor such as reboxetine (including S,S-reboxetine) for narcolepsy (e.g., with cataplexy and/or EDS) may not have, and/or may be selected for not having myocardial infarction. Some patients treated with an antidepressant, including a norepinephrine inhibitor such as reboxetine (including S,S-reboxetine) for narcolepsy (e.g., with cataplexy and/or EDS) may not have, and/or may be selected for not having angina. Some patients treated with an antidepressant, including a norepinephrine inhibitor such as reboxetine (including S,S-reboxetine) for narcolepsy (e.g., with cataplexy and/or EDS) may not have, and/or may be selected for not having dysrhythmias. Some patients treated with an antidepressant, including a norepinephrine inhibitor such as reboxetine (including S,S-reboxetine) for narcolepsy (e.g., with cataplexy and/or EDS) may not have, and/or may be selected for not having cardiac failure.

Some patients treated with an antidepressant, including a norepinephrine inhibitor such as reboxetine (including S,S-reboxetine) for narcolepsy (e.g., with cataplexy and/or EDS) may not have, and/or may be selected for not having a history of narrow angle glaucoma. Some patients treated with an antidepressant, including a norepinephrine inhibitor such as reboxetine (including S,S-reboxetine) for narcolepsy (e.g., with cataplexy and/or EDS) may not have, and/or may be selected for not having gastric bypass. Some patients treated with an antidepressant, including a norepinephrine inhibitor such as reboxetine (including S,S-reboxetine) for narcolepsy (e.g., with cataplexy and/or EDS) may not have, and/or may be selected for not having any condition that would be expected to affect drug absorption.

Some patients treated with an antidepressant, including a norepinephrine inhibitor such as reboxetine (including S,S-reboxetine) for narcolepsy (e.g., with cataplexy and/or EDS) may not have, and/or may be selected for not having, headaches. Some patients treated with an antidepressant, including a norepinephrine inhibitor such as reboxetine (including S,S-reboxetine) for narcolepsy (e.g., with cataplexy and/or EDS) may not have, and/or may be selected for not having, a depression. Some patients treated with an antidepressant, including a norepinephrine inhibitor such as reboxetine (including S,S-reboxetine) for narcolepsy (e.g., with cataplexy and/or EDS) may not have, and/or may be selected for not having, major depression. Some patients treated with an antidepressant, including a norepinephrine inhibitor such as reboxetine (including S,S-reboxetine) for narcolepsy (e.g., with cataplexy and/or EDS) may not have, and/or may be selected for not having, a treatment resistant depression.

Some patients treated with an antidepressant, including a norepinephrine inhibitor such as reboxetine (including S,S-reboxetine) for narcolepsy (e.g., with cataplexy and/or EDS) may not have, and/or may be selected for not having, treatment resistant bipolar depression. Some patients treated with an antidepressant, including a norepinephrine inhibitor such as reboxetine (including S,S-reboxetine) for narcolepsy (e.g., with cataplexy and/or EDS) may not have, and/or may be selected for not having, a bipolar disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, cyclothymia. Some patients treated with an antidepressant, including a norepinephrine inhibitor such as reboxetine (including S,S-reboxetine) for narcolepsy (e.g., with cataplexy and/or EDS) may not have, and/or may be selected for not having, a seasonal affective disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a mood disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, chronic depression (e.g., dysthymia). Some patients treated with an antidepressant, including a norepinephrine inhibitor such as reboxetine (including S,S-reboxetine) for narcolepsy (e.g., with cataplexy and/or EDS) may not have, and/or may be selected for not having, a psychotic depression. Some patients treated with an antidepressant, including a norepinephrine inhibitor such as reboxetine (including S,S-reboxetine) for narcolepsy (e.g., with cataplexy and/or EDS) may not have, and/or may be selected for not having a history of psychotic episodes. Some patients treated with an antidepressant, including a norepinephrine inhibitor such as reboxetine (including S,S-reboxetine) for narcolepsy (e.g., with cataplexy and/or EDS) may not have, and/or may be selected for not having significant risk of self-injury, suicide, or aggression towards others. Some patients treated with an antidepressant, including a norepinephrine inhibitor such as reboxetine (including S,S-reboxetine) for narcolepsy (e.g., with cataplexy and/or EDS) may not have, and/or may be selected for not having, a postpartum depression. Some patients treated with an antidepressant, including a norepinephrine inhibitor such as reboxetine (including S,S-reboxetine) for narcolepsy (e.g., with cataplexy and/or EDS) may not have, and/or may be selected for not having, a premenstrual dysphoric disorder (PMDD). Some patients treated with an antidepressant, including a norepinephrine inhibitor such as reboxetine (including S,S-reboxetine) for narcolepsy (e.g., with cataplexy and/or EDS) may not have, and/or may be selected for not having, a situational depression. Some patients treated with an antidepressant, including a norepinephrine inhibitor such as reboxetine (including S,S-reboxetine) for narcolepsy (e.g., with cataplexy and/or EDS) may not have, and/or may be selected for not having, an atypical depression. Some patients treated with an antidepressant, including a norepinephrine inhibitor such as reboxetine (including S,S-reboxetine) for narcolepsy (e.g., with cataplexy and/or EDS) may not have, and/or may be selected for not having, a mania. Some patients treated with an antidepressant, including a norepinephrine inhibitor such as reboxetine (including S,S-reboxetine) for narcolepsy (e.g., with cataplexy and/or EDS) may not have, and/or may be selected for not having, an anxiety disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, attention deficit disorder (ADD).

Some patients treated with an antidepressant, including a norepinephrine inhibitor such as reboxetine (including S,S-reboxetine) for narcolepsy (e.g., with cataplexy and/or EDS) may not have, and/or may be selected for not having, attention deficit disorder with hyperactivity (ADDH). Some patients treated with an antidepressant, including a norepinephrine inhibitor such as reboxetine (including S,S-reboxetine) for narcolepsy (e.g., with cataplexy and/or EDS) may not have, and/or may be selected for not having, attention deficit/hyperactivity disorder (AD/HD). Some patients treated with an antidepressant, including a norepinephrine inhibitor such as reboxetine (including S,S-reboxetine) for narcolepsy (e.g., with cataplexy and/or EDS) may not have, and/or may be selected for not having, a manic condition. Some patients treated with an antidepressant, including a norepinephrine inhibitor such as reboxetine (including S,S-reboxetine) for narcolepsy (e.g., with cataplexy and/or EDS) may not have, and/or may be selected for not having, an obsessive-compulsive disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a bulimia. Some patients treated with an antidepressant, including a norepinephrine inhibitor such as reboxetine (including S,S-reboxetine) for narcolepsy (e.g., with cataplexy and/or EDS) may not have, and/or may be selected for not having, obesity or weight-gain. Some patients treated with an antidepressant, including a norepinephrine inhibitor such as reboxetine (including S,S-reboxetine) for narcolepsy (e.g., with cataplexy and/or EDS) may not have, and/or may be selected for not having, a chronic fatigue syndrome.

Some patients treated with an antidepressant, including a norepinephrine inhibitor such as reboxetine (including S,S-reboxetine) for narcolepsy (e.g., with cataplexy and/or EDS) may not have, and/or may be selected for not having, a premenstrual syndrome. Some patients treated with an antidepressant, including a norepinephrine inhibitor such as reboxetine (including S,S-reboxetine) for narcolepsy (e.g., with cataplexy and/or EDS) may not have, and/or may be selected for not having, a substance addiction or abuse. Some patients treated with an antidepressant, including a norepinephrine inhibitor such as reboxetine (including S,S-reboxetine) for narcolepsy (e.g., with cataplexy and/or EDS) may not have, and/or may be selected for not having, a nicotine addiction. Some patients treated with an antidepressant, including a norepinephrine inhibitor such as reboxetine (including S,S-reboxetine) for narcolepsy (e.g., with cataplexy and/or EDS) may not have, and/or may be selected for not having, a psycho-sexual dysfunction. Some patients treated with an antidepressant, including a norepinephrine inhibitor such as reboxetine (including S,S-reboxetine) for narcolepsy (e.g., with cataplexy and/or EDS) may not have, and/or may be selected for not having, a pseudobulbar affect. Some patients treated with an antidepressant, including a norepinephrine inhibitor such as reboxetine (including S,S-reboxetine) for narcolepsy (e.g., with cataplexy and/or EDS) may not have, and/or may be selected for not having, emotional lability.

Some patients treated with an antidepressant, including a norepinephrine inhibitor such as reboxetine (including S,S-reboxetine) for narcolepsy (e.g., with cataplexy and/or EDS) may not have, and/or may be selected for not having, an anxiety disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a phobia. Some patients treated with an antidepressant, including a norepinephrine inhibitor such as reboxetine (including S,S-reboxetine) for narcolepsy (e.g., with cataplexy and/or EDS) may not have, and/or may be selected for not having, a generalized anxiety disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a social anxiety disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a panic disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, an agoraphobia. Some patients treated with an antidepressant, including a norepinephrine inhibitor such as reboxetine (including S,S-reboxetine) for narcolepsy (e.g., with cataplexy and/or EDS) may not have, and/or may be selected for not having, an obsessive-compulsive disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, post-traumatic stress disorder (PTSD). Some patients treated with an antidepressant, including a norepinephrine inhibitor such as reboxetine (including S,S-reboxetine) for narcolepsy (e.g., with cataplexy and/or EDS) may not have, and/or may be selected for not having, a mania.

Some patients treated with an antidepressant, including a norepinephrine inhibitor such as reboxetine (including S,S-reboxetine) for narcolepsy (e.g., with cataplexy and/or EDS) may not have, and/or may be selected for not having, a manic depressive illness. Some patients treated with an antidepressant, including a norepinephrine inhibitor such as reboxetine (including S,S-reboxetine) for narcolepsy (e.g., with cataplexy and/or EDS) may not have, and/or may be selected for not having, a hypomania. Some patients treated with an antidepressant, including a norepinephrine inhibitor such as reboxetine (including S,S-reboxetine) for narcolepsy (e.g., with cataplexy and/or EDS) may not have, and/or may be selected for not having, a unipolar depression. Some patients treated with an antidepressant, including a norepinephrine inhibitor such as reboxetine (including S,S-reboxetine) for narcolepsy (e.g., with cataplexy and/or EDS) may not have, and/or may be selected for not having, a stress disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a somatoform disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a personality disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a psychosis.

Some patients treated with an antidepressant, including a norepinephrine inhibitor such as reboxetine (including S,S-reboxetine) for narcolepsy (e.g., with cataplexy and/or EDS) may not have, and/or may be selected for not having, schizophrenia. Some patients treated with an antidepressant, including a norepinephrine inhibitor such as reboxetine (including S,S-reboxetine) for narcolepsy (e.g., with cataplexy and/or EDS) may not have, and/or may be selected for not having, a delusional disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a schizoaffective disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a schizotypy. Some patients treated with an antidepressant, including a norepinephrine inhibitor such as reboxetine (including S,S-reboxetine) for narcolepsy (e.g., with cataplexy and/or EDS) may not have, and/or may be selected for not having, aggression. Some patients treated with an antidepressant, including a norepinephrine inhibitor such as reboxetine (including S,S-reboxetine) for narcolepsy (e.g., with cataplexy and/or EDS) may not have, and/or may be selected for not having, aggression in Alzheimer's disease. Some patients treated with an antidepressant, including a norepinephrine inhibitor such as reboxetine (including S,S-reboxetine) for narcolepsy (e.g., with cataplexy and/or EDS) may not have, and/or may be selected for not having, agitation. Some patients treated with an antidepressant, including a norepinephrine inhibitor such as reboxetine (including S,S-reboxetine) for narcolepsy (e.g., with cataplexy and/or EDS) may not have, and/or may be selected for not having, agitation in Alzheimer's disease.

Some patients treated with an antidepressant, including a norepinephrine inhibitor such as reboxetine (including S,S-reboxetine) for narcolepsy (e.g., with cataplexy and/or EDS) may not have, and/or may be selected for not having, a drug dependence. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to cocaine. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on a psychostimulant. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on crack. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on cocaine. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on speed. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on methamphetamine. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on nicotine.

Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on alcohol. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on an opioid. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on an anxiolytic and/or a hypnotic drug. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on a cannabis (marijuana). Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on an amphetamine. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on a hallucinogen. Some patients treated with an antidepressant, including a norepinephrine inhibitor such as reboxetine (including S,S-reboxetine) for narcolepsy (e.g., with cataplexy and/or EDS) may not have, and/or may be selected for not having, an addiction to or dependence on phencyclidine.

Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on a volatile solvent. Some patients treated with an antidepressant, including a norepinephrine inhibitor such as reboxetine (including S,S-reboxetine) for narcolepsy (e.g., with cataplexy and/or EDS) may not have, and/or may be selected for not having, addiction to or dependence on a volatile nitrite. Some patients treated with an antidepressant, including a norepinephrine inhibitor such as reboxetine (including S,S-reboxetine) for narcolepsy (e.g., with cataplexy and/or EDS) may not have, and/or may be selected for not having, senile dementia. Some patients treated with an antidepressant, including a norepinephrine inhibitor such as reboxetine (including S,S-reboxetine) for narcolepsy (e.g., with cataplexy and/or EDS) may not have, and/or may be selected for not having, an Alzheimer's type dementia. Some patients treated with an antidepressant, including a norepinephrine inhibitor such as reboxetine (including S,S-reboxetine) for narcolepsy (e.g., with cataplexy and/or EDS) may not have, and/or may be selected for not having, memory loss. Some patients treated with an antidepressant, including a norepinephrine inhibitor such as reboxetine (including S,S-reboxetine) for narcolepsy (e.g., with cataplexy and/or EDS) may not have, and/or may be selected for not having, an amnesia/amnestic syndrome. Some patients treated with an antidepressant, including a norepinephrine inhibitor such as reboxetine (including S,S-reboxetine) for narcolepsy (e.g., with cataplexy and/or EDS) may not have, and/or may be selected for not having, an apilepsy. Some patients treated with an antidepressant, including a norepinephrine inhibitor such as reboxetine (including S,S-reboxetine) for narcolepsy (e.g., with cataplexy and/or EDS) may not have, and/or may be selected for not having, disturbances of consciousness.

Some patients treated with an antidepressant, including a norepinephrine inhibitor such as reboxetine (including S,S-reboxetine) for narcolepsy (e.g., with cataplexy and/or EDS) may not have, and/or may be selected for not having, a coma. Some patients treated with an antidepressant, including a norepinephrine inhibitor such as reboxetine (including S,S-reboxetine) for narcolepsy (e.g., with cataplexy and/or EDS) may not have, and/or may be selected for not having, a lowering of attention. Some patients treated with an antidepressant, including a norepinephrine inhibitor such as reboxetine (including S,S-reboxetine) for narcolepsy (e.g., with cataplexy and/or EDS) may not have, and/or may be selected for not having, a speech disorder. Some patients treated with an antidepressant, including a norepinephrine inhibitor such as reboxetine (including S,S-reboxetine) for narcolepsy (e.g., with cataplexy and/or EDS) may not have, and/or may be selected for not having, a voice spasm. Some patients treated with an antidepressant, including a norepinephrine inhibitor such as reboxetine (including S,S-reboxetine) for narcolepsy (e.g., with cataplexy and/or EDS) may not have, and/or may be selected for not having, Parkinson's disease. Some patients treated with an antidepressant, including a norepinephrine inhibitor such as reboxetine (including S,S-reboxetine) for narcolepsy (e.g., with cataplexy and/or EDS) may not have, and/or may be selected for not having, a Lennox-Gastaut syndrome.

Some patients treated with an antidepressant, including a norepinephrine inhibitor such as reboxetine (including S,S-reboxetine) for narcolepsy (e.g., with cataplexy and/or EDS) may not have, and/or may be selected for not having, autism. Some patients treated with an antidepressant, including a norepinephrine inhibitor such as reboxetine (including S,S-reboxetine) for narcolepsy (e.g., with cataplexy and/or EDS) may not have, and/or may be selected for not having, a hyperkinetic syndrome. Some patients treated with an antidepressant, including a norepinephrine inhibitor such as reboxetine (including S,S-reboxetine) for narcolepsy (e.g., with cataplexy and/or EDS) may not have, and/or may be selected for not having, schizophrenia. Some patients treated with an antidepressant, including a norepinephrine inhibitor such as reboxetine (including S,S-reboxetine) for narcolepsy (e.g., with cataplexy and/or EDS) may not have, and/or may be selected for not having, had a stroke. Some patients treated with an antidepressant, including a norepinephrine inhibitor such as reboxetine (including S,S-reboxetine) for narcolepsy (e.g., with cataplexy and/or EDS) may not have, and/or may be selected for not having, a cerebral infarction. Some patients treated with an antidepressant, including a norepinephrine inhibitor such as reboxetine (including S,S-reboxetine) for narcolepsy (e.g., with cataplexy and/or EDS) may not have, and/or may be selected for not having, a cerebral bleeding. Some patients treated with an antidepressant, including a norepinephrine inhibitor such as reboxetine (including S,S-reboxetine) for narcolepsy (e.g., with cataplexy and/or EDS) may not have, and/or may be selected for not having, a cerebral arteriosclerosis. Some patients treated with an antidepressant, including a norepinephrine inhibitor such as reboxetine (including S,S-reboxetine) for narcolepsy (e.g., with cataplexy and/or EDS) may not have, and/or may be selected for not having, a cerebral venous thrombosis. Some patients treated with an antidepressant, including a norepinephrine inhibitor such as reboxetine (including S,S-reboxetine) for narcolepsy (e.g., with cataplexy and/or EDS) may not have, and/or may be selected for not having, a head injury.

Some patients treated with an antidepressant, including a norepinephrine inhibitor such as reboxetine (including S,S-reboxetine) for narcolepsy (e.g., with cataplexy and/or EDS) may not have, and/or may be selected for not having, an akinesia. Some patients treated with an antidepressant, including a norepinephrine inhibitor such as reboxetine (including S,S-reboxetine) for narcolepsy (e.g., with cataplexy and/or EDS) may not have, and/or may be selected for not having, an athetosis. Some patients treated with an antidepressant, including a norepinephrine inhibitor such as reboxetine (including S,S-reboxetine) for narcolepsy (e.g., with cataplexy and/or EDS) may not have, and/or may be selected for not having, an ataxia. Some patients treated with an antidepressant, including a norepinephrine inhibitor such as reboxetine (including S,S-reboxetine) for narcolepsy (e.g., with cataplexy and/or EDS) may not have, and/or may be selected for not having, a ballismus. Some patients treated with an antidepressant, including a norepinephrine inhibitor such as reboxetine (including S,S-reboxetine) for narcolepsy (e.g., with cataplexy and/or EDS) may not have, and/or may be selected for not having, a hemiballismus. Some patients treated with an antidepressant, including a norepinephrine inhibitor such as reboxetine (including S,S-reboxetine) for narcolepsy (e.g., with cataplexy and/or EDS)

may not have, and/or may be selected for not having, a bradykinesia. Some patients treated with an antidepressant, including a norepinephrine inhibitor such as reboxetine (including S,S-reboxetine) for narcolepsy (e.g., with cataplexy and/or EDS) may not have, and/or may be selected for not having, a cerebral palsy.

Some patients treated with an antidepressant, including a norepinephrine inhibitor such as reboxetine (including S,S-reboxetine) for narcolepsy (e.g., with cataplexy and/or EDS) may not have, and/or may be selected for not having, a chorea. Some patients treated with an antidepressant, including a norepinephrine inhibitor such as reboxetine (including S,S-reboxetine) for narcolepsy (e.g., with cataplexy and/or EDS) may not have, and/or may be selected for not having, Huntington's disease. Some patients treated with an antidepressant, including a norepinephrine inhibitor such as reboxetine (including S,S-reboxetine) for narcolepsy (e.g., with cataplexy and/or EDS) may not have, and/or may be selected for not having, a rheumatic chorea. Some patients treated with an antidepressant, including a norepinephrine inhibitor such as reboxetine (including S,S-reboxetine) for narcolepsy (e.g., with cataplexy and/or EDS) may not have, and/or may be selected for not having, a Sydenham's chorea. Some patients treated with an antidepressant, including a norepinephrine inhibitor such as reboxetine (including S,S-reboxetine) for narcolepsy (e.g., with cataplexy and/or EDS) may not have, and/or may be selected for not having, a dyskinesia. Some patients treated with an antidepressant, including a norepinephrine inhibitor such as reboxetine (including S,S-reboxetine) for narcolepsy (e.g., with cataplexy and/or EDS) may not have, and/or may be selected for not having, a tardive dyskinesia. Some patients treated with an antidepressant, including a norepinephrine inhibitor such as reboxetine (including S,S-reboxetine) for narcolepsy (e.g., with cataplexy and/or EDS) may not have, and/or may be selected for not having, a dystonia. Some patients treated with an antidepressant, including a norepinephrine inhibitor such as reboxetine (including S,S-reboxetine) for narcolepsy (e.g., with cataplexy and/or EDS) may not have, and/or may be selected for not having, a blepharospasm.

Some patients treated with an antidepressant, including a norepinephrine inhibitor such as reboxetine (including S,S-reboxetine) for narcolepsy (e.g., with cataplexy and/or EDS) may not have, and/or may be selected for not having, a spasmodic torticollis. Some patients treated with an antidepressant, including a norepinephrine inhibitor such as reboxetine (including S,S-reboxetine) for narcolepsy (e.g., with cataplexy and/or EDS) may not have, and/or may be selected for not having, a dopamine-responsive dystonia. Some patients treated with an antidepressant, including a norepinephrine inhibitor such as reboxetine (including S,S-reboxetine) for narcolepsy (e.g., with cataplexy and/or EDS) may not have, and/or may be selected for not having, restless legs syndrome (RLS). Some patients treated with an antidepressant, including a norepinephrine inhibitor such as reboxetine (including S,S-reboxetine) for narcolepsy (e.g., with cataplexy and/or EDS) may not have, and/or may be selected for not having, a tremor. Some patients treated with an antidepressant, including a norepinephrine inhibitor such as reboxetine (including S,S-reboxetine) for narcolepsy (e.g., with cataplexy and/or EDS) may not have, and/or may be selected for not having, an essential tremor. Some patients treated with an antidepressant, including a norepinephrine inhibitor such as reboxetine (including S,S-reboxetine) for narcolepsy (e.g., with cataplexy and/or EDS) may not have, and/or may be selected for not having, Tourette's syndrome. Some patients treated with an antidepressant, including a norepinephrine inhibitor such as reboxetine (including S,S-reboxetine) for narcolepsy (e.g., with cataplexy and/or EDS) may not have, and/or may be selected for not having, Wilson's disease.

Some patients treated with an antidepressant, including a norepinephrine inhibitor such as reboxetine (including S,S-reboxetine) for narcolepsy (e.g., with cataplexy and/or EDS) may not have, and/or may be selected for not having, a vascular dementia. Some patients treated with an antidepressant, including a norepinephrine inhibitor such as reboxetine (including S,S-reboxetine) for narcolepsy (e.g., with cataplexy and/or EDS) may not have, and/or may be selected for not having, a dementia with Lewy bodies. Some patients treated with an antidepressant, including a norepinephrine inhibitor such as reboxetine (including S,S-reboxetine) for narcolepsy (e.g., with cataplexy and/or EDS) may not have, and/or may be selected for not having, a mixed dementia. Some patients treated with an antidepressant, including a norepinephrine inhibitor such as reboxetine (including S,S-reboxetine) for narcolepsy (e.g., with cataplexy and/or EDS) may not have, and/or may be selected for not having, a fronto-temporal dementia. Some patients treated with an antidepressant, including a norepinephrine inhibitor such as reboxetine (including S,S-reboxetine) for narcolepsy (e.g., with cataplexy and/or EDS) may not have, and/or may be selected for not having, Creutzfeldt-Jakob disease. Some patients treated with an antidepressant, including a norepinephrine inhibitor such as reboxetine (including S,S-reboxetine) for narcolepsy (e.g., with cataplexy and/or EDS) may not have, and/or may be selected for not having, a normal pressure hydrocephalus. Some patients treated with an antidepressant, including a norepinephrine inhibitor such as reboxetine (including S,S-reboxetine) for narcolepsy (e.g., with cataplexy and/or EDS) may not have, and/or may be selected for not having, Wernicke-Korsakoff Syndrome.

Some patients treated with an antidepressant, including a norepinephrine inhibitor such as reboxetine (including S,S-reboxetine) for narcolepsy (e.g., with cataplexy and/or EDS) may not have, and/or may be selected for not having, Pick's disease. Some patients treated with an antidepressant, including a norepinephrine inhibitor such as reboxetine (including S,S-reboxetine) for narcolepsy (e.g., with cataplexy and/or EDS) may not have, and/or may be selected for not having, a progressive bulbar palsy. Some patients treated with an antidepressant, including a norepinephrine inhibitor such as reboxetine (including S,S-reboxetine) for narcolepsy (e.g., with cataplexy and/or EDS) may not have, and/or may be selected for not having, a primary lateral sclerosis (PLS). Some patients treated with an antidepressant, including a norepinephrine inhibitor such as reboxetine (including S,S-reboxetine) for narcolepsy (e.g., with cataplexy and/or EDS) may not have, and/or may be selected for not having, a progressive muscular atrophy. Some patients treated with an antidepressant, including a norepinephrine inhibitor such as reboxetine (including S,S-reboxetine) for narcolepsy (e.g., with cataplexy and/or EDS) may not have, and/or may be selected for not having, a post-polio syndrome (PPS). Some patients treated with an antidepressant, including a norepinephrine inhibitor such as reboxetine (including S,S-reboxetine) for narcolepsy (e.g., with cataplexy and/or EDS) may not have, and/or may be selected for not having, a spinal muscular atrophy (SMA).

Some patients treated with an antidepressant, including a norepinephrine inhibitor such as reboxetine (including S,S-reboxetine) for narcolepsy (e.g., with cataplexy and/or EDS) may not have, and/or may be selected for not having, a spinal motor atrophy. Some patients treated with an antidepressant, including a norepinephrine inhibitor such as reboxetine (including S,S-reboxetine) for narcolepsy (e.g., with cataplexy and/or EDS) may not have, and/or may be selected for not having, Tay-Sach's disease. Some patients treated with an antidepressant, including a norepinephrine inhibitor such as reboxetine (including S,S-reboxetine) for narcolepsy (e.g., with cataplexy and/or EDS) may not have, and/or may be selected for not having, a Sandoff disease. Some patients treated with an antidepressant, including a norepinephrine inhibitor such as reboxetine (including S,S-reboxetine) for narcolepsy (e.g., with cataplexy and/or EDS) may not have, and/or may be selected for not having, a hereditary spastic paraplegia. Some patients treated with an antidepressant, including a norepinephrine inhibitor such as reboxetine (including S,S-reboxetine) for narcolepsy (e.g., with cataplexy and/or EDS) may not have, and/or may be selected for not having, Alzheimer's disease. Some patients treated with an antidepressant, including a norepinephrine inhibitor such as reboxetine (including S,S-reboxetine) for narcolepsy (e.g., with cataplexy and/or EDS) may not have, and/or may be selected for not having, a prion-related disease. Some patients treated with an antidepressant, including a norepinephrine inhibitor such as reboxetine (including S,S-reboxetine) for narcolepsy (e.g., with cataplexy and/or EDS) may not have, and/or may be selected for not having, a cerebellar ataxia. Some patients treated with an antidepressant, including a norepinephrine inhibitor such as reboxetine (including S,S-reboxetine) for narcolepsy (e.g., with cataplexy and/or EDS) may not have, and/or may be selected for not having, a spinocerebellar ataxia (SCA).

Some patients treated with an antidepressant, including a norepinephrine inhibitor such as reboxetine (including S,S-reboxetine) for narcolepsy (e.g., with cataplexy and/or EDS) may not have, and/or may be selected for not having, a spinal muscular atrophy (SMA). Some patients treated with an antidepressant, including a norepinephrine inhibitor such as reboxetine (including S,S-reboxetine) for narcolepsy (e.g., with cataplexy and/or EDS) may not have, and/or may be selected for not having, a bulbar muscular atrophy. Some patients treated with an antidepressant, including a norepinephrine inhibitor such as reboxetine (including S,S-reboxetine) for narcolepsy (e.g., with cataplexy and/or EDS) may not have, and/or may be selected for not having, a Friedrich's ataxia. Some patients treated with an antidepressant, including a norepinephrine inhibitor such as reboxetine (including S,S-reboxetine) for narcolepsy (e.g., with cataplexy and/or EDS) may not have, and/or may be selected for not having, Lewy body disease. Some patients treated with an antidepressant, including a norepinephrine inhibitor such as reboxetine (including S,S-reboxetine) for narcolepsy (e.g., with cataplexy and/or EDS) may not have, and/or may be selected for not having, amyotrophic lateral sclerosis (ALS or Lou Gehrig's disease). Some patients treated with an antidepressant, including a norepinephrine inhibitor such as reboxetine (including S,S-reboxetine) for narcolepsy (e.g., with cataplexy and/or EDS) may not have, and/or may be selected for not having, multiple sclerosis (MS). Some patients treated with an antidepressant, including a norepinephrine inhibitor such as reboxetine (including S,S-reboxetine) for narcolepsy (e.g., with cataplexy and/or EDS) may not have, and/or may be selected for not having, a multiple system atrophy.

Some patients treated with an antidepressant, including a norepinephrine inhibitor such as reboxetine (including S,S-reboxetine) for narcolepsy (e.g., with cataplexy and/or EDS) may not have, and/or may be selected for not having, Shy-Drager syndrome. Some patients treated with an antidepressant, including a norepinephrine inhibitor such as reboxetine (including S,S-reboxetine) for narcolepsy (e.g., with cataplexy and/or EDS) may not have, and/or may be selected for not having, a corticobasal degeneration. Some patients treated with an antidepressant, including a norepinephrine inhibitor such as reboxetine (including S,S-reboxetine) for narcolepsy (e.g., with cataplexy and/or EDS) may not have, and/or may be selected for not having, a progressive supranuclear palsy.

Some patients treated with an antidepressant, including a norepinephrine inhibitor such as reboxetine (including S,S-reboxetine) for narcolepsy (e.g., with cataplexy and/or EDS) may not have, and/or may be selected for not having, Wilson's disease. Some patients treated with an antidepressant, including a norepinephrine inhibitor such as reboxetine (including S,S-reboxetine) for narcolepsy (e.g., with cataplexy and/or EDS) may not have, and/or may be selected for not having, Menkes disease. Some patients treated with an antidepressant, including a norepinephrine inhibitor such as reboxetine (including S,S-reboxetine) for narcolepsy (e.g., with cataplexy and/or EDS) may not have, and/or may be selected for not having, an adrenoleukodystrophy. Some patients treated with an antidepressant, including a norepinephrine inhibitor such as reboxetine (including S,S-reboxetine) for narcolepsy (e.g., with cataplexy and/or EDS) may not have, and/or may be selected for not having, a cerebral autosomal dominant arteriopathy with subcortical infarcts and leukoencephalopathy (CADASIL). Some patients treated with an antidepressant, including a norepinephrine inhibitor such as reboxetine (including S,S-reboxetine) for narcolepsy (e.g., with cataplexy and/or EDS) may not have, and/or may be selected for not having, a muscular dystrophy. Some patients treated with an antidepressant, including a norepinephrine inhibitor such as reboxetine (including S,S-reboxetine) for narcolepsy (e.g., with cataplexy and/or EDS) may not have, and/or may be selected for not having, a Charcot-Marie-Tooth disease (CMT). Some patients treated with an antidepressant, including a norepinephrine inhibitor such as reboxetine (including S,S-reboxetine) for narcolepsy (e.g., with cataplexy and/or EDS) may not have, and/or may be selected for not having, a familial spastic paraparesis. Some patients treated with an antidepressant, including a norepinephrine inhibitor such as reboxetine (including S,S-reboxetine) for narcolepsy (e.g., with cataplexy and/or EDS) may not have, and/or may be selected for not having, a neurofibromatosis. Some patients treated with an antidepressant, including a norepinephrine inhibitor such as reboxetine (including S,S-reboxetine) for narcolepsy (e.g., with cataplexy and/or EDS) may not have, and/or may be selected for not having, an olivopontine cerebellar atrophy or degeneration. Some patients treated with an antidepressant, including a norepinephrine inhibitor such as reboxetine (including S,S-reboxetine) for narcolepsy (e.g., with cataplexy and/or EDS) may not have, and/or may be selected for not having, a striatonigral degeneration. Some patients treated with an antidepressant, including a norepinephrine inhibitor such as reboxetine (including S,S-reboxetine) for narcolepsy (e.g., with cataplexy and/or EDS) may not have, and/or may be selected for not having, Guillain-Barr-syndrome. Some patients treated with an antidepressant, including a norepinephrine inhibitor such as reboxetine (including S,S-reboxetine) for narcolepsy (e.g., with cataplexy and/or EDS) may not have, and/or may be selected for not having, a spastic paraplesia. Some patients treated with an antidepressant, including a norepinephrine inhibitor such as reboxetine (including S,S-reboxetine) for narcolepsy (e.g., with cataplexy and/or EDS) may not have, and/or may be selected for not having, epileptic seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, nonepileptic seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, epilepsy. Some patients treated with an antidepressant, including a norepinephrine inhibitor such as reboxetine (including S,S-reboxetine) for narcolepsy (e.g., with cataplexy and/or EDS) may not have, and/or may be selected for not having, febrile seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, partial seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, simple partial seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, Jacksonian seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, complex partial seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, an epilepsia partialis continua. Some patients treated with an antidepressant, including a norepinephrine inhibitor such as reboxetine (including S,S-reboxetine) for narcolepsy (e.g., with cataplexy and/or EDS) may not have, and/or may be selected for not having, generalized seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, generalized tonic-clonic seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, an absence seizure.

Some patients treated with an antidepressant, including a norepinephrine inhibitor such as reboxetine (including S,S-reboxetine) for narcolepsy (e.g., with cataplexy and/or EDS) may not have, and/or may be selected for not having, atonic seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, myoclonic seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, juvenile myoclonic seizures. Some patients treated with an antidepressant, including a norepinephrine inhibitor such as reboxetine (including S,S-reboxetine) for narcolepsy (e.g., with cataplexy and/or EDS) may not have, and/or may be selected for not having, infantile spasm. Some patients treated with an antidepressant, including a norepinephrine inhibitor such as reboxetine (including S,S-reboxetine) for narcolepsy (e.g., with cataplexy and/or EDS) may not have, and/or may be selected for not having, status epilepticus. Some patients treated with an antidepressant, including a norepinephrine inhibitor such as reboxetine (including S,S-reboxetine) for narcolepsy (e.g., with cataplexy and/or EDS) may not have, and/or may be selected for not having, Rett Syndrome. Some patients treated with an antidepressant, including a norepinephrine inhibitor such as reboxetine (including S,S-reboxetine) for narcolepsy (e.g., with cataplexy and/or EDS) may not have, and/or may be selected for not having, a tinnitus. Some patients treated with an antidepressant, including a norepinephrine inhibitor such as reboxetine (including S,S-reboxetine) for narcolepsy (e.g., with cataplexy and/or EDS) may not have, and/or may be selected for not having, disturbances of consciousness disorders. Some patients treated with an antidepressant, including a norepinephrine inhibitor such as reboxetine (including S,S-reboxetine) for narcolepsy (e.g., with cataplexy and/or EDS) may not have, and/or may be selected for not having, a sexual dysfunction. Some patients treated with an antidepressant, including a norepinephrine inhibitor such as reboxetine (including S,S-reboxetine) for narcolepsy (e.g., with cataplexy and/or EDS) may not have, and/or may be selected for not having, a voice disorder due to uncontrolled laryngeal muscle spasms. Some patients treated with an antidepressant, including a norepinephrine inhibitor such as reboxetine (including S,S-reboxetine) for narcolepsy (e.g., with cataplexy and/or EDS) may not have, and/or may be selected for not having, an abductor spasmodic dysphonia. Some patients treated with an antidepressant, including a norepinephrine inhibitor such as reboxetine (including S,S-reboxetine) for narcolepsy (e.g., with cataplexy and/or EDS) may not have, and/or may be selected for not having, an adductor spasmodic dysphonia. Some patients treated with an antidepressant, including a norepinephrine inhibitor such as reboxetine (including S,S-reboxetine) for narcolepsy (e.g., with cataplexy and/or EDS) may not have, and/or may be selected for not having, a muscular tension dysphonia. Some patients treated with an antidepressant, including a norepinephrine inhibitor such as reboxetine (including S,S-reboxetine) for narcolepsy (e.g., with cataplexy and/or EDS) may not have, and/or may be selected for not having, a vocal tremor. Some patients treated with an antidepressant, including a norepinephrine inhibitor such as reboxetine (including S,S-reboxetine) for narcolepsy (e.g., with cataplexy and/or EDS) may not have, and/or may be selected for not having, a diabetic neuropathy. Some patients treated with an antidepressant, including a norepinephrine inhibitor such as reboxetine (including S,S-reboxetine) for narcolepsy (e.g., with cataplexy and/or EDS) may not have, and/or may be selected for not having, a chemotherapy-induced neurotoxicity. Some patients treated with an antidepressant, including a norepinephrine inhibitor such as reboxetine (including S,S-reboxetine) for narcolepsy (e.g., with cataplexy and/or EDS) may not have, and/or may be selected for not having, methotrexate neurotoxicity. Some patients treated with an antidepressant, including a norepinephrine inhibitor such as reboxetine (including S,S-reboxetine) for narcolepsy (e.g., with cataplexy and/or EDS) may not have, and/or may be selected for not having, a stress urinary incontinence. Some patients treated with an antidepressant, including a norepinephrine inhibitor such as reboxetine (including S,S-reboxetine) for narcolepsy (e.g., with cataplexy and/or EDS) may not have, and/or may be selected for not having, urge urinary incontinence. Some patients treated with an antidepressant, including a norepinephrine inhibitor such as reboxetine (including S,S-reboxetine) for narcolepsy (e.g., with cataplexy and/or EDS) may not have, and/or may be selected for not having, fecal incontinence. Some patients treated with an antidepressant, including a norepinephrine inhibitor such as reboxetine (including S,S-reboxetine) for narcolepsy (e.g., with cataplexy and/or EDS) may not have, and/or may be selected for not having, erectile dysfunction.

Cataplexy includes a sudden reduction or loss of muscle tone while a patient is awake, which may affect specific parts of the body or the entire body, such as eyelids, head drop, facial sagging and/or twitching, slurred speech, jaw weakness, weakness in arms, shoulders, or hands, and/or buckling of knees. Cataplexy may be pathognomonic for narcolepsy. Cataplexy may be triggered by strong emotions, such as laughter, elation, surprise, or anger. Cataplexy may be partial or localized (in about 75% of cases) and is usually of short duration. The frequency of cataplexy may vary widely. Narcolepsy with cataplexy may be socially disabling and isolating.

Some patients being treated with an antidepressant, including a norepinephrine inhibitor such as reboxetine (including S,S-reboxetine) may have, and/or may be selected for having, narcolepsy with cataplexy (Type 1) that is an autoimmune disorder resulting in a loss of hypocretin (orexin)-producing neurons in the CNS. Hypocretins (orexins) are hypothalamic-specific peptides with neuroexcitatory activity. A patient being treated with an antidepressant, including a norepinephrine inhibitor such as reboxetine (including S,S-reboxetine) for narcolepsy with cataplexy is, and may be selected for being, a predisposed individual with specific genetic markers including human leukocyte antigen (HLA DQB1/06:02) and/or T-cell receptor alpha variants. Some patients being treated with an antidepressant, including a norepinephrine inhibitor such as reboxetine (including S,S-reboxetine) may not have, and may be selected for not having, narcolepsy associated with loss of hypocretin neurons. Some patients being treated with an antidepressant, including a norepinephrine inhibitor such as reboxetine (including S,S-reboxetine) may have, or may be selected for having, narcolepsy precipitated by seasonal *Streptococcus* infections, H1N1 influenza, and/or H1N1 vaccination in genetically predisposed individuals.

Existing treatments for narcolepsy only address some of its symptoms, provide variable efficacy, and have significant side effects. Additionally, all existing treatments are controlled substances.

According to the FDA, "there is a continued need for additional effective and tolerable treatment options for patients to improve their daily functioning." (*The Voice of the Patient, A series of reports from the U.S. Food and Drug Administration's (FDA's) Patient-Focused Drug Development Initiative, Narcolepsy*, June 2014. p. 25)

In some embodiments, administering an antidepressant, including a norepinephrine inhibitor such as reboxetine (including S,S-reboxetine) may reduce daytime sleepiness by at least about 1%, at least about 5%, at least about 10%, at least about 20%, at least about 30%, at least about 40%, at least about 50%, at least about 60%, at least about 70%, at least about 80%, at least about 90%, about 1-5%, about 5-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. as compared to baseline, placebo, or some other appropriate control (including an active control, such as a stimulant (e.g. methylphenidate, an amphetamine), modafinil, armodafinil, sodium oxybate, a tricyclic antidepressant, a selective serotonin reuptake inhibitor (SSRI), or a selective norepinephrine reuptake inhibitor (SNRI)). This improvement may be observed at e.g., 1 week, 2 weeks, overall, or at any other relevant time, such as 1 month, 6 months, 1 year, 2 years, etc. of the treatment with reboxetine.

In some embodiments, administering an antidepressant, including a norepinephrine inhibitor such as reboxetine (including S,S-reboxetine) may reduce cataplexy by at least about 1%, at least about 5%, at least about 10%, at least about 20%, at least about 30%, at least about 40%, at least about 50%, at least about 60%, at least about 70%, at least about 80%, at least about 90%, about 1-5%, about 5-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine.

In some embodiments, administering an antidepressant, including a norepinephrine inhibitor such as reboxetine (including S,S-reboxetine) may reduce the number of partial cataplexy attacks by at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 40-45%, about 45-50%, about 50-60%, about 60-70%, about 70-80%, about 80-90%, about 90-100%, about 1-25%, about 25-50%, about 50-75%, or about 75-100%, at least about 1 per week, at least about 2 per week, at least about 3 per week, at least about 4 per week, at least about 5 per week, at least about 6 per week, at least about 7 per week, at least about 8 per week, at least about 9 per week, at least about 10 per week, at least about 12 per week, at least about 13 per week, at least about 14 per week, at least about 15 per week, at least about 16 per week, at least about 18 per week, at least about 20 per week, at least about 22 per week, at least about 24 per week, at least about 26 per week, at least about 28 per week, at least about 30 per week, at least about 40 per week, at least about 50 per week, about 1-2 per week, about 2-3 per week, about 3-4 per week, about 4-5 per week, about 5-6 per week, about 6-7 per week, about 7-8 per week, about 8-9 per week, about 9-10 per week, about 10-11 per week, about 11-12 per week, about 12-13 per week, about 13-14 per week, about 14-15 per week, about 15-16 per week, about 16-17 per week, about 17-18 per week, about 18-19 per week, about 19-20 per week, about 1-10 per week, about 10-20 per week, about 20-30 per week, about 30-40 per week, about 40-50 per week, about 50-60 per week, or more, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant ($p \leq 0.05$) as compared with administering a placebo. This improvement may be rapid. For example, at or within one week of the treatment with reboxetine in human beings, the average reduction in cataplexy attacks may be at least about 10%, about 10-20%, about 20-30%, about 30-40%, about 40-50%, about 40-45%, about 45-50%, or about 50-60%.

In some embodiments, administering an antidepressant, including a norepinephrine inhibitor such as reboxetine (including S,S-reboxetine) may reduce the number of complete cataplexy attacks by at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 40-45%, about 45-50%, about 50-60%, about 60-70%, about 70-80%, about 80-90%, about 90-100%, about 1-25%, about 25-50%, about 50-75%, or about 75-100%, at least about 1 per week, at least about 2 per week, at least about 3 per week, at least about 4 per week, at least about 5 per week, at least about 6 per week, at least about 7 per week, at least about 8 per week, at least about 9 per week, at least about 10 per week, at least about 12 per week, at least about 13 per week, at least about 14 per week, at least about 15 per week, at least about 16 per week, at least about 18 per week, at least about 20 per week, at least about 22 per week, at least about 24 per week, at least about 26 per week, at least about 28 per week, at least about 30 per week, at least about 40 per week, at least about 50 per week, about 1-2 per week, about 2-3 per week, about 3-4 per week, about 4-5 per week, about 5-6 per week, about 6-7 per week, about 7-8 per week, about 8-9 per week, about 9-10 per week, about 10-11 per week, about 11-12 per week, about 12-13 per week, about 13-14 per week, about 14-15 per week, about 15-16 per week, about 16-17 per week, about 17-18 per week, about 18-19 per week, about 19-20 per week, about 1-10 per week, about 10-20 per week, about 20-30 per week, about 30-40 per week, about 40-50 per week, about 50-60 per week, or more, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant (p≤0.05) as compared with administering a placebo. This improvement may be rapid. For example, at or within one week of the treatment with reboxetine in human beings, the average reduction in cataplexy attacks may be at least about 10%, about 10-20%, about 20-30%, about 30-40%, about 40-50%, about 40-45%, about 45-50%, or about 50-60%.

In some embodiments, administering an antidepressant, including a norepinephrine inhibitor such as reboxetine (including S,S-reboxetine) may reduce the total number of cataplexy attacks (partial+complete) by at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 40-45%, about 45-50%, about 50-60%, about 60-70%, about 70-80%, about 80-90%, about 90-100%, about 1-25%, about 25-50%, about 50-75%, about 75-100%, about 40-60%, at least about 1 per week, at least about 2 per week, at least about 3 per week, at least about 4 per week, at least about 5 per week, at least about 6 per week, at least about 7 per week, at least about 8 per week, at least about 9 per week, at least about 10 per week, at least about 12 per week, at least about 13 per week, at least about 14 per week, at least about 15 per week, at least about 16 per week, at least about 18 per week, at least about 20 per week, at least about 22 per week, at least about 24 per week, at least about 26 per week, at least about 28 per week, at least about 30 per week, at least about 40 per week, at least about 50 per week, at least about 60 per week, at least about 70 per week, at least about 80 per week, at least about 90 per week, at least about 100 per week, at least about 110 per week, at least about 120 per week, at least about 130 per week, at least about 140 per week, about 10-20 per week, about 12-18 per week, about 14-16 per week, about 1-2 per week, about 2-3 per week, about 3-4 per week, about 4-5 per week, about 5-6 per week, about 6-7 per week, about 7-8 per week, about 8-9 per week, about 9-10 per week, about 10-11 per week, about 11-12 per week, about 12-13 per week, about 13-14 per week, about 14-15 per week, about 15-16 per week, about 16-17 per week, about 17-18 per week, about 18-19 per week, about 19-20 per week, about 1-10 per week, about 10-20 per week, about 20-30 per week, about 30-40 per week, about 40-50 per week, about 50-60 per week, about 60-70 per week, about 70-80 per week, about 80-90 per week, about 90-100 per week, about 100-120 per week, about 120-140 per week, or more, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant (p≤0.05) as compared with administering a placebo. This improvement may be rapid. For example, at or within one week of the treatment with reboxetine in human beings, the average reduction in cataplexy attacks may be at least about 10%, about 10-20%, about 20-30%, about 30-40%, about 40-50%, about 40-45%, about 45-50%, or about 50-60%.

In some embodiments, administering an antidepressant, including a norepinephrine inhibitor such as reboxetine (including S,S-reboxetine) may result in the proportion of patients achieving a 50% or greater reduction in the weekly number of cataplexy attacks that is about 40-50%, about 50-60%, about 50-55%, 55-60%, about 60-70%, about 60-95%, about 70-80%, about 70-75%, about 75-80%, or about 74-78%, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant (p≤0.05) as compared with administering a placebo.

In some embodiments, administering an antidepressant, including a norepinephrine inhibitor such as reboxetine (including S,S-reboxetine) may result in the proportion of patients achieving a 75% or greater reduction in the weekly number of cataplexy attacks that is about 15-20%, about 20-30%, about 20-25%, about 25-30%, about 30-40%, about 40-50%, about 40-45%, about 45-50%, about 50-60%, about 60-70%, about 60-95%, or about 70-80%, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant (p≤0.05) as compared with administering a placebo.

In some embodiments, administering an antidepressant, including a norepinephrine inhibitor such as reboxetine (including S,S-reboxetine) may reduce the Epworth Sleepiness Scale (ESS) score by at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, about 24, about 1-2, about 2-3, about 3-4, about 4-5, about 5-6, about 6-7, about 7-8, about 8-9, about 9-10, about 10-11, about 11-12, about 12-13, about 13-14, about 14-15, about 15-16, about 16-17, about 17-18, about 18-19, about 19-20, about 20-21, about 21-22, about 22-23, about 23-24, about 1-4, about 4-8, about 8-12, about 12-16, about 16-20, about 20-24, about 1-12, or about 12-24 e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant as compared with administering a placebo with p value of ≤0.05, 0.01-0.05, <0.01, 0.005-0.01, 0.001-0.005, or about 0.003.

In some embodiments, administering an antidepressant, including a norepinephrine inhibitor such as reboxetine (including S,S-reboxetine) may reduce the weekly number of inadvertent naps by at least about at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, about 75-100%, about 20-40%, about 30-35%, or about 30-33%, at least about 1 nap per week, at least about 2 naps per week, at least about 3 naps per week, at least about 4 naps per week, at least about 5 naps per week, about 1-3 naps per week, about 2-4 naps per week, about 3-4 napes per week, about 3-5 naps per week, about 4-6 naps per week, about 5-6 naps per week, e.g. as compared to baseline, placebo, or some other appropriate control (including an active control, such as a stimulant (e.g. methylphenidate, an amphetamine), modafinil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant as compared with administering a placebo with p value of ≤0.05, 0.03-0.05, 0.01-0.05, <0.01, 0.005-0.01, 0.001-0.005, about 0.003, or <0.001. A patient may be selected for treatment based upon having a problem with inadvertent naps, such as inadvertent naps associated with narcolepsy (with or without cataplexy).

In some embodiments, administering an antidepressant, including a norepinephrine inhibitor such as reboxetine (including S,S-reboxetine) may result in the proportion of patients achieving a 50% or greater reduction in the weekly number of inadvertent naps that is about 15-20%, about 20-30%, about 30-40%, about 30-35%, about 35-40%, about 40-50%, about 50-60%, about 60-70%, or about 70-80%, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant (p≤0.05) as compared with administering a placebo.

In some embodiments, administering an antidepressant, including a norepinephrine inhibitor such as reboxetine (including S,S-reboxetine) may reduce the Maintenance of Wakefulness Test (MWT) score by at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, at least about 15 minutes, at least about 16 minutes, at least about 17 minutes, at least about 18 minutes, at least about 19 minutes, at least about 20 minutes, about 1-2 minutes, about 2-3 minutes, about 3-4 minutes, about 4-5 minutes, about 5-6 minutes, about 6-7 minutes, about 7-8 minutes, about 8-9 minutes, about 9-10 minutes, about 10-11 minutes, about 11-12 minutes, about 12-13 minutes, about 13-14 minutes, about 14-15 minutes, about 15-16 minutes, about 16-17 minutes, about 17-18 minutes, about 18-19 minutes, about 19-20 minutes, about 20-21 minutes, about 21-22 minutes, about 22-23 minutes, about 23-24 minutes, about 24-26 minutes, about 1-4 minutes, about 4-8 minutes, about 8-12 minutes, about 12-16 minutes, about 16-20 minutes, about 1-10 minutes, or about 10-20 minutes, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine.

In some embodiments, administering an antidepressant, including a norepinephrine inhibitor such as reboxetine (including S,S-reboxetine) may improve cognitive function, e.g., over a 1-week period or a 2-week period, as measured by the Ability to Concentrate item of the NSAQ. For example, the improvement in the ability to concentrate score on a 5-point scale (1=very good, 2=good, 3=average, 4=poor, and 5=very poor) may be at least about −0.1, at least about −0.2, at least about −0.3, about −0.05 to about −0.5, about −0.05 to about −0.2, about −0.2 to about −0.3, about 0.3 to about −0.4, about −0.4 to about −0.5, about −0.5 to −0.6, about −0.6 to about −0.7, or about −0.7 to about −0.8, e.g., as compared to baseline, placebo, or some other appropriate control (including an active control, such as a stimulant (e.g., methylphenidate, an amphetamine), modafanil, armodafanil, sodium oxybate, a tricyclic antidepressant, an SSRI, or an SNRI), wherein "-" represents reduction in the ability to concentrate score. In some embodiments, the number of patients having an ability to concentrate that is "very good" or "good" may be at least about 20%, at least 25%, at least about 30%, at least about 40%, at least about 50%, at least about 60%, at least about 70%, at least about 80%, at least about 90%, at least about 95%, about 20-30%, about 30-40%, about 30-35%, about 35-40%, about 40-50%, about 40-45%, about 45-50%, about 50-60%, about 60-70%, about 70-80%, about 80-90%, about 90-100%, about 1-25%, about 15-25%, about 25-50%, about 50-75%, or about 75-100%, about 40-60%, about 35-40%, or about 40-45%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant (p≤0.05) as compared with administering a placebo, e.g., p=0.01-0.05, <0.01, 0.001-0.01, 0.001-0.005, 0.005-0.01, 0.002 or 0.007. A patient may be selected for treatment based upon having reduced cognitive function, such as reduced cognitive function associated with narcolepsy (with or without cataplexy).

In some embodiments, prior to the start of treatment, the human being has an ability to concentrate that is "average," "poor," or "very poor," and one week after the start of the treatment, the human being has an ability to concentrate that is "good" or "very good."

In some embodiments, prior to the start of treatment, the human being has an ability to concentrate that is "average," and one week after the start of the treatment, the human being has an ability to concentrate that is "good."

In some embodiments, prior to the start of treatment, the human being has an ability to concentrate that is "average," and one week after the start of the treatment, the human being has an ability to concentrate that is "very good."

In some embodiments, prior to the start of treatment, the human being has an ability to concentrate that is "poor," and one week after the start of the treatment, the human being has an ability to concentrate that is "good."

In some embodiments, prior to the start of treatment, the human being has an ability to concentrate that is "poor," and one week after the start of the treatment, the human being has an ability to concentrate that is "very good."

In some embodiments, prior to the start of treatment, the human being has an ability to concentrate that is "very poor," and one week after the start of the treatment, the human being has an ability to concentrate that is "good."

In some embodiments, prior to the start of treatment, the human being has an ability to concentrate that is "very poor," and one week after the start of the treatment, the human being has an ability to concentrate that is "very good."

In some embodiments, prior to the start of treatment, the human being has an ability to concentrate that is "average," "poor," or "very poor," and two weeks after the start of the treatment, the human being has an ability to concentrate that is "good" or "very good."

In some embodiments, prior to the start of treatment, the human being has an ability to concentrate that is "average," and two weeks after the start of the treatment, the human being has an ability to concentrate that is "good."

In some embodiments, prior to the start of treatment, the human being has an ability to concentrate that is "average," and two weeks after the start of the treatment, the human being has an ability to concentrate that is "very good."

In some embodiments, prior to the start of treatment, the human being has an ability to concentrate that is "poor," and two weeks after the start of the treatment, the human being has an ability to concentrate that is "good."

In some embodiments, prior to the start of treatment, the human being has an ability to concentrate that is "poor," and two weeks after the start of the treatment, the human being has an ability to concentrate that is "very good."

In some embodiments, prior to the start of treatment, the human being has an ability to concentrate that is "very poor," and two weeks after the start of the treatment, the human being has an ability to concentrate that is "good."

In some embodiments, prior to the start of treatment, the human being has an ability to concentrate that is "very poor," and two weeks after the start of the treatment, the human being has an ability to concentrate that is "very good."

In some embodiments, administering an antidepressant, including a norepinephrine inhibitor such as reboxetine (including S,S-reboxetine) may improve sleep quality. For example, the patient may report improved sleep quality. In some embodiments, the number of patients reporting improved sleep quality may be at least about 20%, at least about 30%, at least about 40%, at least about 50%, at least about 60%, at least about 70%, at least about 80%, at least about 90%, at least about 95%, about 20-30%, about 30-40%, about 40-50%, about 50-60%, about 60-70%, about 70-80%, about 80-90%, about 90-100%, about 1-25%, about 25-50%, about 50-75%, or about 75-100%, about 40-60%, about 42-47%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). In some embodiments, a patient may have an improvement in sleep quality that is at least about 20%, at least about 30%, at least about 40%, at least about 50%, at least about 60%, at least about 70%, at least about 80%, at least about 90%, at least about 95%, about 10-20%, about 20-30%, about 30-40%, about 40-50%, about 40-45%, about 45-40%, about 50-60%, about 60-70%, about 70-80%, about 80-90%, about 90-100%, about 1-25%, about 25-50%, about 50-75%, or about 75-100%, about 40-60%, about 42-47%, or about 45%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant (p≤0.05) as compared with administering a placebo, e.g., p=0.01-0.05, <0.01, 0.001-0.01, 0.001-0.005, 0.005-0.01, or 0.007. A patient may be selected for treatment based upon having a problem with sleep quality, such as a problem with sleep quality associated with narcolepsy (with or without cataplexy).

In some embodiments, administering an antidepressant, including a norepinephrine inhibitor such as reboxetine (including S,S-reboxetine) may reduce the number of awakenings at night, e.g., as reported by the patient. For example, the number of patients reporting a reduction in the number of awakenings at night may be at least about 20%, at least about 30%, at least about 40%, at least about 50%, at least about 60%, at least about 70%, at least about 80%, at least about 90%, at least about 95%, about 20-30%, about 30-40%, about 40-50%, about 50-60%, about 60-70%, about 70-80%, about 80-90%, about 90-100%, about 1-25%, about 25-50%, about 50-75%, or about 75-100%, about 40-60%, about 42-47%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). In some embodiments, a patient may have a reduction in the number of awakenings at night that is at least about 20%, at least about 30%, at least about 40%, at least about 50%, at least about 60%, at least about 70%, at least about 80%, at least about 90%, at least about 95%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, about 40-60%, about 42-47%, or about 30%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. This improvement with the treatment of reboxetine may be statistically significant (p≤0.05) as compared with administering a placebo, e.g., p=0.01-0.05, 0.04-0.05, or 0.044. A patient may be selected for treatment based upon having a problem with awakenings at night, such as a problem with awakenings at night associated with narcolepsy (with or without cataplexy).

In some embodiments, administering an antidepressant, including a norepinephrine inhibitor such as reboxetine (including S,S-reboxetine) may reduce the number of sleep paralysis episodes, e.g., as reported by the patient. For example, the number of patients having a reduction in the number of sleep paralysis episodes may be at least about 20%, at least about 30%, at least about 40%, at least about 50%, at least about 60%, at least about 70%, at least about 80%, at least about 90%, at least about 95%, about 20-30%, about 30-40%, about 40-50%, about 50-60%, about 60-70%, about 70-80%, about 80-90%, about 90-100%, about 1-25%, about 25-50%, about 50-75%, or about 75-100%, about 50-70%, about 52-57%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). In some embodiments, a patient may have a reduction in the number of sleep paralysis episodes that is at least about 20%, at least about 30%, at least about 40%, at least about 50%, at least about 60%, at least about 70%, at least about 80%, at least about 90%, at least about 95%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, about 50-70%, about 52-57%, or about 55%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. A patient may be selected for treatment based upon having a problem with sleep paralysis, such as a problem with sleep paralysis associated with narcolepsy (with or without cataplexy).

In some embodiments, administering an antidepressant, including a norepinephrine inhibitor such as reboxetine (including S,S-reboxetine) may reduce the number of hypnagogic hallucinations, e.g., as reported by the patient. For example, the number of patients having a reduction in the number of hypnagogic hallucinations may be at least about 10%, at least about 20%, at least about 30%, at least about 40%, about 20-30%, about 30-40%, about 40-50%, about 50-60%, about 60-70%, about 70-80%, about 80-90%, about 90-100%, about 1-25%, about 25-50%, about 50-75%, or about 75-100%, about 30-50%, about 35-45%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). In some embodiments, a patient may have a reduction in the number of hypnagogic hallucinations that is at least about 10%, at least about 20%, at least about 30%, at least about 40%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, about 30-50%, about 35-45%, or about 40%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. A patient may be selected for treatment based upon problems with hypnagogic hallucinations, such as hypnagogic hallucinations associated with narcolepsy (with or without cataplexy).

In some embodiments, administering an antidepressant, including a norepinephrine inhibitor such as reboxetine (including S,S-reboxetine) may reduce the cataplexy score on the UNS by at least about 10%, at least about 20%, at least about 30%, at least about 40%, at least about 45%, at least about 50%, at least about 60%, at least about 70%, at least about 80%, at least about 90%, at least about 95%, about 1-10%, about 10-20%, about 20-30%, about 30-40%, about 40-50%, about 45-50%, about 50-60%, about 60-70%, about 70-80%, about 80-90%, about 90-100%, about 1-25%, about 25-50%, about 50-75%, or about 75-100%, at least about 1, at least about 2, at least about 3, at least about 4, at least about 5, at least about 6, at least about 7, at least about 8, at least about 9, at least about 10, about 11, about 2-3, about 3-4, about 4-5, about 5-6, about 6-7, about 7-8, about 8-9, about 9-10, about 2-4, about 4-6, about 6-8, about 8-10, about 10-11, about 2-6, or about 6-10, about 5-11, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. In some embodiments, administering an antidepressant, including a norepinephrine inhibitor such as reboxetine (including S,S-reboxetine) may increase sleep latency on the MSLT by at least about 30%, at least about 50%, at least about 60%, at least about 70%, at least about 80%, at least about 90%, at least about 95%, about 50-60%, more than 55%, about 60-70%, about 70-80%, about 80-90%, about 90-100%, about 50-75%, or about 75-100%, at least about 1 minute, at least about 2 minutes, at least about 3 minutes, more than 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, at least about 15 minutes, at least about 16 minutes, at least about 17 minutes, at least about 18 minutes, at least about 19 minutes, at least about 20 minutes, about 1-2 minutes, about 2-3 minutes, about 3-4 minutes, about 4-5 minutes, about 5-6 minutes, about 6-7 minutes, about 7-8 minutes, about 8-9 minutes, about 9-10 minutes, about 10-11 minutes, about 11-12 minutes, about 12-13 minutes, about 13-14 minutes, about 14-15 minutes, about 15-16 minutes, about 16-17 minutes, about 17-18 minutes, about 18-19 minutes, about 19-20 minutes, about 1-4 minutes, about 4-8 minutes, about 8-12 minutes, about 12-16 minutes, about 16-20 minutes, about 1-10 minutes, or about 10-20 minutes, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine.

In some embodiments, administering an antidepressant, including a norepinephrine inhibitor such as reboxetine (including S,S-reboxetine) may reduce the Patient Global Impression of Severity (PGI-S) score by at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, about 75-100%, at least about 0.1, at least about 0.5, at least about 1, at least about 1.5, at least about 2, at least about 2.5, at least about 3, at least about 3.5, about 0.1-0.5, about 0.5-1, about 1-1.5, about 1.5-2, about 2-2.5, about 2.5-3, about 3-3.5, or about 3.5-4, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine.

In some embodiments, administering an antidepressant, including a norepinephrine inhibitor such as reboxetine (including S,S-reboxetine) may result in a Patient Global Impression of Change (PGI-C) score that is about 1-2, about 2-3, or about 3-4, or is reduced by at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, about 75-100%, at least about 0.5, at least about 1, at least about 2, at least about 3, at least about 4, at least about 5, about 0.5-1, about 1-2, about 2-3, about 3-4, about 4-5, or about 5-6, e.g. as compared to placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine.

In some embodiments, administering an antidepressant, including a norepinephrine inhibitor such as reboxetine (including S,S-reboxetine) may reduce the Hamilton Depression Rating Scale (HAM-D) score by at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 30, at least about 40, about 1-2, about 2-3, about 3-4, about 4-5, about 5-6, about 6-7, about 7-8, about 8-9, about 9-10, about 10-11, about 11-12, about 12-13, about 13-14, about 14-15, about 15-16, about 16-17, about 17-18, about 18-19, about 19-20, about 20-21, about 21-22, about 22-23, about 23-27, about 27-30, about 30-35, about 35-40, about 40-45, about 45-50, about 1-4, about 4-8, about 8-12, about 12-16, about 16-20, about 20-24, about 24-30, about 30-40, about 40-50, about 1-12, about 12-24, about 24-36, or about 36-50 e.g., as compared to baseline, placebo, or some other appropriate control (including an active control, such as a stimulant (e.g., methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine.

In some embodiments, administering an antidepressant, including a norepinephrine inhibitor such as reboxetine (including S,S-reboxetine) may reduce nightmares or unpleasant dreams (such as frequent nightmares and frequent unpleasant dreams) by at least about 1%, at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. as compared to baseline, placebo, or some other appropriate control (including an active control, such as a stimulant (e.g. methylphenidate, an amphetamine), modafinil, armodafinil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. A patient may be selected for treatment based upon having a problem with nightmares or unpleasant dreams (such as frequent nightmares and frequent unpleasant dreams), including nightmares or unpleasant dreams (such as frequent nightmares and frequent unpleasant dreams) associated with narcolepsy (with or without cataplexy).

In some embodiments, administering an antidepressant, including a norepinephrine inhibitor such as reboxetine (including S,S-reboxetine) may reduce hallucinations by at least about 1%, at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. A patient may be selected for treatment based upon having a problem with hallucinations, such as hallucinations associated with narcolepsy (with or without cataplexy).

In some embodiments, administering an antidepressant, including a norepinephrine inhibitor such as reboxetine (including S,S-reboxetine) may reduce sleep paralysis by at least about 1%, at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. A patient may be selected for treatment based upon having a problem with sleep paralysis, such as sleep paralysis associated with narcolepsy (with or without cataplexy).

In some embodiments, administering an antidepressant, including a norepinephrine inhibitor such as reboxetine (including S,S-reboxetine) may reduce disturbed nocturnal sleep by at least about 1%, at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. A patient may be selected for treatment based upon having a problem with disturbed nocturnal sleep, such as disturbed nocturnal sleep associated with narcolepsy (with or without cataplexy).

In some embodiments, administering an antidepressant, including a norepinephrine inhibitor such as reboxetine (including S,S-reboxetine) may reduce narcolepsy-related accidents by at least about 1%, at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. A patient may be selected for treatment based upon having a problem with narcolepsy-related accidents (with or without cataplexy).

In some embodiments, administering an antidepressant, including a norepinephrine inhibitor such as reboxetine (including S,S-reboxetine) may reduce narcolepsy-related injuries by at least about 1%, at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine.

In some embodiments, administering an antidepressant, including a norepinephrine inhibitor such as reboxetine (including S,S-reboxetine) may reduce narcolepsy-related fatal accidents by at least about 1%, at least about 10%, at least about 20%, at least about 30%, at least about 40%, at least about 50%, at least about 60%, at least about 70%, at least about 80%, at least about 90%, at least about 95%, about 1-10%, about 10-20%, about 20-30%, about 30-40%, about 40-50%, about 50-60%, about 60-70%, about 70-80%, about 80-90%, about 90-100%, about 1-25%, about 25-50%, about 50-75%, or about 75-100%, e.g. as compared to baseline, placebo, or some other appropriate control (including an active control, such as a stimulant (e.g. methylphenidate, an amphetamine), modafanil, armodafanil, sodium oxybate, a tricyclic antidepressant, an SSRI, or an SNRI). This improvement may be observed at e.g., 1 week, 2 weeks, overall, or at any other relevant time, such as 1 month, 6 months, 1 year, 2 years, etc. of the treatment with reboxetine. A patient may be selected for treatment based upon being at risk for narcolepsy-related fatal accidents (for narcolepsy patients with or without cataplexy).

Reboxetine (with the structure shown below) (including S,S-reboxetine, e.g., with the structure shown below) is a highly selective and potent norepinephrine reuptake inhibitor that has the potential to address the key symptoms of narcolepsy, such as cataplexy or EDS. Unlike existing treatments for narcolepsy, reboxetine is not a controlled substance. Thus, the treatment with reboxetine would not be scheduled.

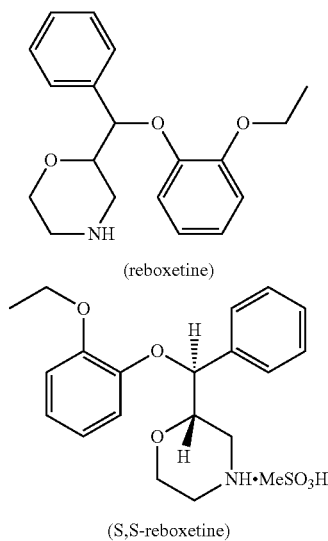

(reboxetine)

(S,S-reboxetine)

Unless otherwise indicated, any reference to a compound herein, such as reboxetine, by structure, name, or any other means, includes pharmaceutically acceptable salts; free acids or bases; alternate solid forms, such as polymorphs, solvates, hydrates, etc.; tautomers; enantiomers; deuterium modified compounds, such as deuterium modified reboxetine; or any chemical species that may rapidly convert to a compound described herein under conditions in which the compounds are used as described herein.

In some embodiments, reboxetine is in a salt form, a free base form, or may contain an excess (e.g., at least 60%, at least 70%, at least 80%, at least 90%, at least 95%, at least 97%, or at least 99%) of (+)-reboxetine, also referred to as S,S-reboxetine or esreboxetine; or an excess (e.g., at least 60%, at least 70%, at least 80%, at least 90%, at least 95%, at least 97%, or at least 99%) of (−)-reboxetine.

For treatment of narcolepsy, the reboxetine (including S,S-reboxetine) may be administered in a manner that results in 1) a first local maximum in reboxetine (including S,S-reboxetine) plasma concentration and 2) a second local maximum in reboxetine (including S,S-reboxetine) plasma concentration.

There are many potential ways that reboxetine (including S,S-reboxetine) could be administered in a manner that results in a first local maximum in reboxetine (including S,S-reboxetine) plasma concentration and a second local maximum in reboxetine (including S,S-reboxetine) plasma concentration. A local maximum described herein is a maximum of a plasma concentration in a time period of interest in an individual patient, which is not necessarily the $C_{max}$. The local maximum may be lower or the same as $C_{max}$. One potential way to administer reboxetine (including S,S-reboxetine) in a manner that results in a first local maximum in reboxetine (including S,S-reboxetine) plasma concentration and a second local maximum in reboxetine (including S,S-reboxetine) plasma concentration is to administer a first dosage form containing reboxetine (including S,S-reboxetine) and, at a later time, a second dosage form containing reboxetine (including S,S-reboxetine). The doses are administered at times that result in a first local maximum in reboxetine (including S,S-reboxetine) plasma concentration and a second local maximum in reboxetine (including S,S-reboxetine) plasma concentration. For example, the second dosage form may be administered less than half a day after the first dosage form, e.g. about 1-8 hours, about 8-12 hours, about 2-6 hours, about 1-2 hours, about 2-3 hours, about 3-4 hours, about 4-5 hours, about 5-6 hours, about 6-7 hours, about 7-8 hours, about 1-3 hours, about 2-4 hours, about 3-5 hours, about 4-6 hours, about 5-7 hours, about 6-8 hours, or about 7-10 hours, after the first dosage form, or any time period in a range bounded by any of these values.

Another method involves administering a single dosage form comprising a first release component and a second release component. Both the first release component and the second release component comprise reboxetine (including S,S-reboxetine).

In some embodiments, the first dosage form administered in a day, the only dosage form administered during the day, or the first of two or more dosage forms administered during the day, is administered shortly after waking, such as within about 3 hours, within about 2 hours, within about 1.5 hours, within about 1 hour, within about 30 minutes, or within about 15 minutes of waking from an overnight sleep.

For a single dosage form comprising a first release component and a second release component that is administered in a day, the first release component may release reboxetine (including S,S-reboxetine), may begin releasing reboxetine (including S,S-reboxetine), or may result in a first local maximum in the plasma concentration of reboxetine (including S,S-reboxetine), about 0-30 minutes, about 30-60 minutes, about 60-90 minutes, or about 90-120 minutes after the dosage form is orally administered, or any time period in a range bounded by any of these values. The second release component may release reboxetine (including S,S-reboxetine) after the first release component releases reboxetine (including S,S-reboxetine), or may cause an increase of reboxetine (including S,S-reboxetine) plasma concentration or a second local maximum in the plasma concentration of reboxetine (including S,S-reboxetine), that is about 1-10 hours, about 2-6 hours, about 1-2 hours, about 2-3 hours, about 3-4 hours, about 4-5 hours, about 5-6 hours, about 6-7 hours, about 1-3 hours, about 2-4 hours, about 3-5 hours, about 4-6 hours, about 5-7 hours, about 6-8 hours, or about 7-10 hours after reboxetine (including S,S-reboxetine) is first released from the first release component, or after the first local maximum in the plasma concentration of reboxetine (including S,S-reboxetine), or at any time in a range bounded by any of these values.

The first release component and the second release component may be incorporated into one single dosage form (such as a pill, tablet, capsule, caplet, or cachou). In one embodiment, the first release component would be located in one of the outer layers of the dosage form and the second release component would be located in one of the inner layers of the same dosage form.

In another embodiment, the first release component is located in a first layer of the dosage form, and the second release component is located in a second layer of the same dosage form. The two layers are distinct and may or may not be in contact with one another. In some embodiments, the two layers are stacked on top of one another and physically bound in a bi-layer structure (e.g., where the largest surfaces of the two layers contact one another, or the layers are thin compared to the other dimensions of the layers). In some embodiments, the two layers are positioned next to one another and physically bound in a bi-layer structure (e.g., where the layers are thicker than other dimensions of the layers).

In another embodiment, the first release component and the second release component may be constructed separately in their own specific granules, particles, or the like, wherein the first release component particles are formulated to release reboxetine (including S,S-reboxetine) before the second release component particles release reboxetine (including S,S-reboxetine) and wherein both the first release component particles and the second release component particles are combined together into a single dosage form, such as a capsule, pill, tablet, caplet, cachou or the like, and the two release components may or may not be physically bound to one another.

In some embodiments, the first local maximum plasma concentration of reboxetine (including S,S-reboxetine) occurs about 1-30 minutes, about 30-60 minutes, about 1-2 hours, about 2-3 hours, or about 3-4 hours after the single dosage form or the first dosage form is administered, or at any time in a range bounded by any of these values. Generally, the second local maximum plasma concentration of reboxetine (including S,S-reboxetine) occurs less than half a day after the first local maximum plasma concentration of reboxetine (including S,S-reboxetine), such as about 1-10 hours, about 1-2 hours, about 2-6 hours, about 2-3 hours, about 3-4 hours, about 4-5 hours, about 5-6 hours, about 6-7 hours, about 7-8 hours, about 1-3 hours, about 2-4 hours, about 3-5 hours, about 4-6 hours, about 5-7 hours, about 6-8 hours, or about 7-10 hours, after the first local maximum plasma concentration of reboxetine (including S,S-reboxetine), or any time period in a range bounded by any of these values.

For dosage forms containing a first release component and a second release component, the first release component is associated with the first local maximum in reboxetine (including S,S-reboxetine) plasma concentration in that the first release component releases the reboxetine (including S,S-reboxetine) that contributes to the first local maximum in reboxetine (including S,S-reboxetine) plasma concentration. For example, the first release component could release reboxetine (including S,S-reboxetine) faster or sooner than the second release component, so that most of the reboxetine (including S,S-reboxetine) contributing to the first local maximum plasma concentration of reboxetine (including S,S-reboxetine) that was released from the first release component.

For dosage forms containing a first release component and a second release component, the second release component is associated with the second local maximum in reboxetine (including S,S-reboxetine) plasma concentration in that the second release component releases the reboxetine (including S,S-reboxetine) that contributes to the second local maximum in reboxetine (including S,S-reboxetine) plasma concentration. For example, the second release component could delay release of its reboxetine (including S,S-reboxetine) so that at a time when the reboxetine (including S,S-reboxetine) plasma concentration is decreasing after the first local maximum, the second release component releases a sufficient amount of reboxetine (including S,S-reboxetine) to again increase the plasma concentration of reboxetine (including S,S-reboxetine) so that the second local maximum in reboxetine (including S,S-reboxetine) plasma concentration is achieved.

For dosage forms containing a first release component and a second release component, any suitable amount of reboxetine (including S,S-reboxetine) may be present in the first release component, such as about 1-10 mg, about 0.1-2 mg, about 0.5-1.5 mg, about 1-2 mg, about 1.5-2.5 mg, about 2-3 mg, about 2.5-3.5 mg, about 3-4 mg, about 3.5-4.5 mg, about 4-5 mg, about 4.5-5.5 mg, about 5-6 mg, about 6-7 mg, about 7-8 mg, about 8-9 mg, about 9-10 mg, about 1-3 mg, about 2-4 mg, about 3-5 mg, about 4-6 mg, about 5-7 mg, about 7-10 mg, about 4 mg, about 5 mg, about 0.0003-0.006 mmol, about 0.006-0.009 mmol, about 0.009-0.012 mmol, about 0.012-0.015 mmol, about 0.015-0.018 mmol, about 0.018-0.021 mmol, about 0.021-0.024 mmol, about 0.024-0.027 mmol, about 0.027-0.03 mmol, about 0.03-0.033 mmol, or any amount in a range bounded by any of these values.

For dosage forms containing a first release component and a second release component, any suitable amount of reboxetine (including S,S-reboxetine) may be present in the second release component, such as about 0.1-2 mg, about 0.5-1.5 mg, about 1-3 mg, about 1-2 mg, about 1.5-2.5 mg, about 2-3 mg, about 2.5-3.5 mg, about 3-4 mg, about 2-4 mg, about 3-5 mg, about 3.5-4.5 mg, about 4-5 mg, about 4.5-5.5 mg, about 5-6 mg, about 4-6 mg, about 6-7 mg, about 7-8 mg, about 8-9 mg, about 9-10 mg, about 5-7 mg, about 7-10 mg, about 4 mg, about 5 mg, about 0.0003-0.006 mmol, about 0.006-0.009 mmol, about 0.009-0.012 mmol, about 0.012-0.015 mmol, about 0.015-0.018 mmol, about 0.018-0.021 mmol, about 0.021-0.024 mmol, about 0.024-0.027 mmol, about 0.027-0.03 mmol, about 0.03-0.033 mmol, or any amount in a range bounded by any of these values.

In some embodiments, the first release component may contain more reboxetine (including S,S-reboxetine) than the second release component, such as about 10-20% more, about 20-30% more, or about 30-40% more reboxetine (including S,S-reboxetine), than the second release component.

While the dosing schedules given above may be useful in many situations, the daily dosing schedule may be different than described above. For example, a once a day dose may be administered. A twice daily dose may be administered in any suitable way, such as in the morning and the evening, in a manner described above, or some other way.

In some embodiments, the daily dose of reboxetine (including S,S-reboxetine), may be about 0.5-1 mg, about 1-1.5 mg, about 1.5-2 mg, about 1-2 mg, about 2-3 mg, about 3-4 mg, about 4-5 mg, about 5-6 mg, about 6-7 mg, about 7-8 mg, about 8-9 mg, about 9-10 mg, about 10-11 mg, about 11-12 mg, about 12-13 mg, about 13-14 mg, about 14-15 mg, about 15-16 mg, about 16-17 mg, about 2-5 mg, about 5-8 mg, about 8-11 mg, about 11-14 mg, about 14-17 mg, about 17-20 mg, about 8-10 mg, about 8-12 mg, about 0.0015-0.003 mmol, about 0.003-0.0045 mmol, about 0.0045-0.006 mmol, about 0.003-0.006 mmol, about 0.006-0.009 mmol, about 0.009-0.012 mmol, about 0.012-0.015 mmol, about 0.015-0.018 mmol, about 0.018-0.021 mmol, about 0.021-0.024 mmol, about 0.024-0.027 mmol, about 0.027-0.03 mmol, about 0.03-0.033 mmol, about 0.033-0.036 mmol, about 0.036-0.039 mmol, about 0.039-0.042 mmol, about 0.042-0.045 mmol, about 0.045-0.048 mmol, about 0.048-0.051 mmol, about 0.051-0.054 mmol, about 0.054-0.057 mmol, about 0.057-0.06 mmol, about 0.06-0.063 mmol, about 0.063-0.066 mmol, about 0.066-0.069 mmol, about 0.006-0.01 mmol, about 0.01-0.02 mmol, about 0.02-0.03 mmol, about 0.03-0.04 mmol, about 0.04-0.05 mmol, about 0.05-0.06 mmol, about 0.06-0.07 mmol, or about 0.07-0.08 mmol. The daily dose is the total amount of reboxetine administered in a single day. The daily dose may be administered for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least 4 months, at least 5 months, at least about 6 months, at least about 7 months, at least about 8 months, at least about 9 months, at least about 10 months, at least about 11 months, at least about 12 months, at least 1.5 years, at least 2 years, at least about 3 years, at least about 4 years, at least about 5 years, at least about 10 years, at least about 20 years, or longer. In some embodiments, the daily dose is administered for up to about 6 months, up to about 1 year, up to about 2 years, up to about 5 years, up to about 10 years, up to about 20 years, up to about 40 years, up to about 60 years, or up to about 90 years.

The dose of reboxetine (including S,S-reboxetine) may gradually increase over time, such as for 1, 2, 3, 4, 5, 6, or 7 days, to a maintenance dose, which is a total dose given each day (e.g., a 10 mg maintenance dose could be a once daily 10 mg dose, a 6 mg morning dose and a 4 mg afternoon dose, or 5 mg given twice a day for a total of 10 mg per day). In some embodiments, the maintenance dose may be 2-3 mg, about 3-4 mg, about 4-5 mg, about 5-6 mg, about 6-7 mg, about 7-8 mg, about 8-9 mg, about 9-10 mg, about 10-11 mg, about 11-12 mg, about 12-13 mg, about 13-14 mg, about 14-15 mg, about 15-16 mg, about 16-17 mg, about 2-5 mg, about 5-8 mg, about 8-11 mg, about 11-14 mg, about 14-17 mg, about 17-20 mg, about 8-10 mg, about 8-12 mg, about 0.006-0.009 mmol, about 0.009-0.012 mmol, about 0.012-0.015 mmol, about 0.015-0.018 mmol, about 0.018-0.021 mmol, about 0.021-0.024 mmol, about 0.024-0.027 mmol, about 0.027-0.03 mmol, about 0.03-0.033 mmol, about 0.033-0.036 mmol, about 0.036-0.039 mmol, about 0.039-0.042 mmol, about 0.042-0.045 mmol, about 0.045-0.048 mmol, about 0.048-0.051 mmol, about 0.051-0.054 mmol, about 0.054-0.057 mmol, about 0.057-0.06 mmol, about 0.06-0.063 mmol, about 0.063-0.066 mmol, about 0.066-0.069 mmol, about 0.006-0.01 mmol, about 0.01-0.02 mmol, about 0.02-0.03 mmol, about 0.03-0.04 mmol, about 0.04-0.05 mmol, about 0.05-0.06 mmol, about 0.06-0.07 mmol, or about 0.07-0.08 mmol. In some embodiments, a first dose, e.g., administered in the morning, may contain more reboxetine (including S,S-reboxetine) than a second dose administered in a day, e.g., administered in the afternoon. For example, the first dose of the day, e.g., administered in the morning, may have about 10-20% more, about 20-30% more, or about 30-40% more reboxetine (including S,S-reboxetine) than the second dose of the day, e.g., administered in the afternoon. The maintenance dose may be administered for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least 4 months, at least 5 months, at least about 6 months, at least about 7 months, at least about 8 months, at least about 9 months, at least about 10 months, at least about 11 months, at least about 12 months, at least 1.5 years, at least 2 years, at least about 3 years, at least about 4 years, at least about 5 years, at least about 10 years, at least about 20 years, or longer. In some embodiments, the maintenance dose is administered for up to about 6 months, up to about 1 year, up to about 2 years, up to about 5 years, up to about 10 years, up to about 20 years, up to about 40 years, up to about 60 years, or up to about 90 years.

In some embodiments, a patient receives about 110-130 mg of reboxetine (including S,S-reboxetine) over a period of two weeks.

In some embodiments, the first release component provides immediate release of reboxetine (including S,S-reboxetine). In some embodiments, the first release component provides delayed release of reboxetine (including S,S-reboxetine). In some embodiments, the first release component provides sustained release of reboxetine (including S,S-reboxetine).

In some embodiments, the second release component provides immediate release of reboxetine (including S,S-reboxetine). In some embodiments, the second release component provides delayed release of reboxetine (including S,S-reboxetine). In some embodiments, the second release component provides sustained release of reboxetine (including S,S-reboxetine).

In some embodiments, the first release component provides immediate release of reboxetine (including S,S-reboxetine), and the second release component provides delayed release of reboxetine (including S,S-reboxetine). In some embodiments, the first release component provides immediate release of reboxetine (including S,S-reboxetine), and the second release component provides sustained release of reboxetine (including S,S-reboxetine).

With respect to methods wherein the reboxetine (including S,S-reboxetine) is administered in a first dosage form containing reboxetine (including S,S-reboxetine) and a second dosage form containing reboxetine (including S,S-reboxetine), any suitable amount of reboxetine (including S,S-reboxetine) may be present in the first dosage form, such as about 1-10 mg, about 0.1-1 mg, about 0.1-2 mg, about 0.5-1.5 mg, about 1-3 mg, about 1-2 mg, about 1.5-2.5 mg, about 2-3 mg, about 2.5-3.5 mg, about 3-4 mg, about 3.5-4.5 mg, about 4-5 mg, about 4.5-5.5 mg, about 5-6 mg, about 6-7 mg, about 7-8 mg, about 8-9 mg, about 9-10 mg, about 2-4 mg, about 3-5 mg, about 4-6 mg, about 5-7 mg, about 7-10 mg, about 4 mg, about 5 mg, about 0.0003-0.006 mmol, about 0.006-0.009 mmol, about 0.009-0.012 mmol, about 0.012-0.015 mmol, about 0.015-0.018 mmol, about 0.018-0.021 mmol, about 0.021-0.024 mmol, about 0.024-0.027 mmol, about 0.027-0.03 mmol, about 0.03-0.033 mmol, or any amount in a range bounded by any of these values.

With respect to methods wherein the reboxetine (including S,S-reboxetine) is administered in a first dosage form containing reboxetine (including S,S-reboxetine) and a second dosage form containing reboxetine (including S,S-reboxetine), any suitable amount of reboxetine (including S,S-reboxetine) may be present in the second dosage form, such as about 0.1-1 mg, about 0.1-2 mg, about 0.5-1.5 mg, about 1-3 mg, about 1-2 mg, about 1.5-2.5 mg, about 2-3 mg, about 2.5-3.5 mg, about 3-4 mg, about 3.5-4.5 mg, about 4-5 mg, about 4.5-5.5 mg, about 5-6 mg, about 6-7 mg, about 7-8 mg, about 8-9 mg, about 9-10 mg, about 2-4 mg, about 3-5 mg, about 4-6 mg, about 5-7 mg, about 7-10 mg, about 4 mg, about 5 mg, about 0.0003-0.006 mmol, about 0.006-0.009 mmol, about 0.009-0.012 mmol, about 0.012-0.015 mmol, about 0.015-0.018 mmol, about 0.018-0.021 mmol, about 0.021-0.024 mmol, about 0.024-0.027 mmol, about 0.027-0.03 mmol, about 0.03-0.033 mmol, or any amount in a range bounded by any of these values.

In some embodiments, the first dosage form may contain more reboxetine (including S,S-reboxetine) than the dosage form, such as about 10-20% more, about 20-30% more, or about 30-40% more reboxetine (including S,S-reboxetine) than the second dosage form.

In some embodiments, the first dosage form provides immediate release of reboxetine (including S,S-reboxetine). In some embodiments, the first dosage form provides delayed release of reboxetine (including S,S-reboxetine). In some embodiments, the first dosage form provides sustained release of reboxetine (including S,S-reboxetine).

In some embodiments, the second dosage form provides immediate release of reboxetine (including S,S-reboxetine). In some embodiments, the second dosage form provides delayed release of reboxetine (including S,S-reboxetine). In some embodiments, the second dosage form provides sustained release of reboxetine (including S,S-reboxetine).

With respect to single dosage forms containing both a first release component and a second release component, in some embodiments, the single dosage is administered within two hours of waking from an overnight sleep.

For some embodiments wherein more than one dosage form is given, the first dosage form may be administered within two hours of waking from an overnight sleep.

There are many factors that can affect the overall time required for a drug substance such as reboxetine (including S,S-reboxetine) to be fully absorbed and/or reach a maximum plasma concentration in a human being. Some of these factors include a human patient's age, weight, gender, level of stress, stomach contents, stomach pH level, and the presence of other medications. The time required to reach a maximum plasma concentration of the drug such as reboxetine (including S,S-reboxetine) may also be affected by the time of the day taken the drug such as reboxetine (including S,S-reboxetine) and the level of physical activity of the human patient. Another factor that can affect the time required to reach a maximum plasma concentration of the drug such as reboxetine (including S,S-reboxetine) is the presence or absence of a controlled release coating on the drug such as reboxetine (including S,S-reboxetine).

Controlled release includes: immediate release of drug substance such as reboxetine (including S,S-reboxetine) at a certain time or in a certain area of the body; delayed release of a drug substance; sustained release of drug substance at a certain time or place in the body; or an extended release of a drug substance such as reboxetine (including S,S-reboxetine).

Reboxetine (including S,S-reboxetine) is normally rapidly absorbed in human patients, reaching a maximum plasma concentration in about 2-4 hours. To achieve a delay in the time required to reach a maximum plasma concentration, a controlled release coating or mixture may be employed.

Delayed release is a general drug delivery term that describes the form of an oral medication that does not immediately discharge its active drug component in the mouth or in the stomach of a patient. While there may be many ways to achieve delayed release, delayed release of reboxetine (including S,S-reboxetine) may be achieved by completely or partially surrounding the reboxetine (including S,S-reboxetine), e.g., in the second release component, with a coating or layer (e.g., an inner controlled release coating) that does not immediately dissolve when swallowed. For example, the material of the coating or layer may slowly dissolve in the stomach, and/or slowly disintegrate by chemical reaction, such as by hydrolysis, in the stomach until the layer can no longer prevent the reboxetine (including S,S-reboxetine) from coming into contact with the gastric fluid.

In some embodiments, the delayed release coating ensures delivery through the stomach and into the intestines. Once in the duodenum, the coating may begin to break down and begin to release reboxetine (including S,S-reboxetine). In some cases, the reboxetine (including S,S-reboxetine) may be completely released in the duodenum. In some embodiments, the reboxetine (including S,S-reboxetine) may be partially released in the duodenum, and partially released in the jejunum. In some cases, the reboxetine (including S,S-reboxetine) may be completely released in the jejunum. In some cases, the reboxetine (including S,S-reboxetine) may be partially released in the jejunum and partially released in the ilium. In some cases, the reboxetine (including S,S-reboxetine) may be completely released in the ilium. In some cases, the reboxetine (including S,S-reboxetine) may be partially released in the duodenum, the jejunum, and the ilium. In some embodiments, the reboxetine (including S,S-reboxetine) may be partially released in the ilium, and partially released in the colon. In some cases, the reboxetine (including S,S-reboxetine) may be completely released in the colon.

The time of the delayed release, e.g., between release of the first reboxetine (including S,S-reboxetine) component and the second reboxetine (including S,S-reboxetine) component, can be adjusted by using a material that dissolves or disintegrates more or less slowly in the digestive system, adjusting the thickness of the coating layer or the coating material (e.g., a thicker layer would provide a longer time), and/or by using materials whose properties are sensitive to pH. For example, materials that are less stable to, or more soluble in, acidic pHs, may dissolve or disintegrate more quickly in the stomach because the stomach pH is lower than the pH in the intestines. Conversely, materials that are stable at low pH, but less stable at higher pH may dissolve or disintegrate later because of the time it takes the dosage form to travel through the gastrointestinal tract.

A controlled release formulation containing reboxetine (including S,S-reboxetine) can be coated with one or more functional or non-functional coatings. Examples of functional coatings include controlled release polymeric coatings (i.e., controlled release coats), moisture barrier coatings, enteric polymeric coatings, and the like.

A controlled release polymer may be used for both sustained release or for delayed release, depending upon the structure of the dosage form. For example, interspersing the reboxetine (including S,S-reboxetine) throughout a controlled release polymer can provide sustained release, since the drug will be released for as long as the polymer is present in the GI tract. Delayed release may be achieved by creating a barrier, such as a coating, which is intended to last for a shorter time (e.g., less than 12 hours, less than 10 hours, less than 6 hours, less than 3 hours, etc.), so that when the barrier is penetrated, the reboxetine (including S,S-reboxetine) is freely released. The thickness of the barrier can be used to control the delay time.

Any suitable controlled release polymer may be used, such as acrylic acid and methacrylic acid copolymers and various esters thereof, e.g., methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid) (anhydride), polyacrylamide, poly(methacrylic acid anhydride), and glycidyl methacrylate copolymers.

Other suitable controlled release polymers include polymerizable quaternary ammonium compounds, e.g., quaternized aminoalkyl esters and aminoalkyl amides of acrylic acid and methacrylic acid, for example β-methacryloxyethyltrimethylammonium methosulfate, β-acryloxypropyltrimethylammonium chloride, and trimethylaminomethylmethacrylamide methosulfate. The quaternary ammonium atom can also be part of a heterocycle, as in methacryloxyethyl-methylmorpholinium chloride or the corresponding piperidinium salt, or it can be joined to an acrylic acid group or a methacrylic acid group by way of a group containing hetero atoms, such as a polyglycol ether group. Further suitable polymerizable quaternary ammonium compounds include quaternized vinyl-substituted nitrogen heterocycles such as methyl-vinyl pyridinium salts, vinyl esters of quaternized amino carboxylic acids, styryltrialkyl ammonium salts, and the like. Other polymerizable quaternary ammonium compounds include benzyldimethylammoniumethylmethacrylate chloride, diethylmethylammoniumethyl-acrylate and -methacrylate methosulfate, N-trimethylammoniumpropyl-methacrylamide chloride, and N-trimethylammonium-2,2-dimethylpropyl-1-methacrylate chloride.

Delayed release may also be achieved by using a controlled release polymer that targets a particular pH, with the understanding that, with proper fasting or feeding, the particular pH could correspond to a particular time after administration.

For some controlled release polymers, an acrylic or methacrylic polymer comprises one or more ammonio methacrylate copolymers. Ammonio methacrylate copolymers (such as those sold by Evonik under the trademark EUDRAGIT® RS and RL) are fully polymerized copolymers of acrylic and methacrylic acid esters with a low content of quaternary ammonium groups. The ammonium groups are appended to the ester portion of the methacrylate (as 2-trimethylammonium-ethyl esters). The charged ammonium groups in these polymers make them insoluble and highly permeable with pH-independent swelling. These properties make these polymers useful for customized, time-controlled release of the coated drug. In order to obtain a desirable dissolution profile for a given therapeutically active agent, such as reboxetine (including S,S-reboxetine), two or more ammonio methacrylate copolymers having differing physical properties can be incorporated. For example, it is known that by changing the molar ratio of the pre-polymerized materials containing quaternary ammonium groups to pre-polymerized materials containing the uncharged, neutral methacrylic or acrylic esters, the permeability properties of the resultant coating can be modified.

In other embodiments, the control releasing coat further includes a polymer whose permeability is pH dependent, such as anionic polymers synthesized from methacrylic acid and methacrylic acid methyl ester. Such polymers are commercially available, e.g., from Evonik, under the tradename EUDRAGIT® L and EUDRAGIT® S. The ratio of free carboxyl groups to the esters is known to be 1:1 in EUDRAGIT® L and 1:2 in EUDRAGIT® S. EUDRAGIT® L is insoluble in acids and pure water but becomes increasingly permeable above pH 5.0. This makes EUDRAGIT® L appropriate for targeting release of the coated drug substance such as coated reboxetine (including S,S-reboxetine) in the duodenum and the jejunum of the small intestine. Thus, a EUDRAGIT® L coated drug substance may achieve a delay in maximum plasma concentration, relative to an uncoated or immediate release drug substance (e.g., reboxetine (including S,S-reboxetine) in a first release component), of about 30 min to about 1 hour, about 1-1.5 hours, about 1.5-2 hours, about 2-2.5 hours, about 2.5-3 hours, or about 3.5-4 hours.

EUDRAGIT® S is similar to EUDRAGIT® L, except that it becomes increasingly permeable above pH 7. This makes EUDRAGIT® S appropriate for targeting release of the coated drug substance such as coated reboxetine (including S,S-reboxetine) in the ileum of the small intestine and also the colon. Thus, a EUDRAGIT® S coated drug substance may achieve a delay in maximum plasma concentration, relative to an uncoated or immediate release drug substance (e.g., reboxetine (including S,S-reboxetine) in a first release component), of about 1-2 hours, about 2-3 hours, about 3-4 hours about 4-5 hours, about 5-6 hours, about 6-7 hours, about 7-8 hours, about 8-9 hours, or about 9-10 hours.

A hydrophobic acrylic polymer coating can also include a polymer which is based on dimethylaminoethyl methacrylate and neutral methacrylic acid esters (such as EUDRAGIT® E, commercially available from Evonik). EUDRAGIT® E is not soluble in saliva (making it useful for taste and odor masking) but is soluble in gastric fluid with pH 5 or less, which provides an immediate release of drug product in the stomach. Reboxetine (including S,S-reboxetine) surrounded with a EUDRAGIT® E coating may release reboxetine (including S,S-reboxetine), may begin releasing reboxetine (including S,S-reboxetine), or may reach a first local maximum in the plasma concentration of reboxetine (including S,S-reboxetine), at a time of about 0-30 minutes, 30-60 minutes, 60-90 minutes, or 90-120 minutes after the dosage form is orally administered, or any time period in a range bounded by any of these values.

A hydrophobic acrylic polymer coating can include a neutral copolymer based on a poly methacrylate, such as EUDRAGIT® NE (NE=neutral ester), commercially available from Evonik. EUDRAGIT® NE 30D lacquer films are insoluble in water and digestive fluids, but permeable and swellable, providing another option for time-controlled release. EUDRAGIT® NE has a pH-independent sustained release effect that can release a drug substance such as reboxetine (including S,S-reboxetine) over a period of time, or may delay release for a period of time, wherein the time of release or delay is about 1-24 hours, about 1-18 hours, about 1-12 hours, about 1-8 hours, or about 1-6 hours.

In some embodiments, the control releasing coat comprises a polymer comprising ethyl acrylate and methyl methacrylate in a 2:1 ratio (KOLLICOAT® EMM 30 D, BASF). KOLLICOAT® EMM 30 D has a pH-independent sustained release effect that can release a drug substance such as reboxetine (including S,S-reboxetine) over a period of time, or may delay release for a period of time, wherein the time of release or delay is about 1-24 hours, about 1-18 hours, about 1-12 hours, about 1-8 hours, or about 1-6 hours.

In some embodiments, the control releasing coat comprises a polyvinyl acetate stabilized with polyvinylpyrrolidone and sodium lauryl sulfate such as KOLLICOAT® SR30D (BASF). The dissolution profile can be altered by changing the relative amounts of different acrylic resin lacquers included in the coating. Also, by changing the molar ratio of polymerizable permeability-enhancing agent (e.g., the quaternary ammonium compounds) to the neutral methacrylic esters, the permeability properties (which affect the dissolution profile) of the resultant coating can be modified. KOLLICOAT® SR30D is another coating with a pH-independent sustained release effect that can release a drug substance such as reboxetine (including S,S-reboxetine) over a period of time, or may delay release for a period of time, wherein the time of release or delay is about 1-24 hours, about 1-18 hours, about 1-12 hours, about 1-8 hours, about 1-6 hours, about 1-4 hours, or about 1-2 hours.

In some embodiments, the control releasing coat comprises ethylcellulose, which can be used as a dry polymer (such as ETHOCEL™, Dow Chemical Company) solubilized in organic solvent prior to use, or as an aqueous dispersion. One suitable commercially-available aqueous dispersion of ethylcellulose is Aquacoat® (Danisco). Aquacoat® ECD (ethylcellulose aqueous dispersion), Aquacoat® ARC (alcohol-resistant ethylcellulose aqueous dispersion), and Aquacoat® CPD (cellulose acetate phthalate aqueous dispersion) are all commercially available controlled release coatings. Another suitable aqueous dispersion of ethylcellulose is commercially available as Surelease® (Colorcon, Inc.). This product can be prepared by incorporating plasticizer into the dispersion during the manufacturing process. A hot melt of a polymer, plasticizer (e.g., dibutyl sebacate), and stabilizer (e.g., oleic acid) may be mixed and prepared as a homogeneous mixture, which is then diluted with an alkaline solution to obtain an aqueous dispersion which can be applied directly onto substrates. These coatings have a pH-independent sustained release effect that can release a drug substance such as reboxetine (including S,S-reboxetine) over a period of time, or may delay release for a period of time, wherein the time of release or delay is about 1-24 hours, about 1-18 hours, about 1-12 hours, about 1-8 hours, about 1-6 hours, about 1-4 hours, or about 1-2 hours.

Other examples of polymers that can be used in the control-releasing coat include cellulose acetate phthalate, cellulose acetate trimaleate, hydroxypropyl methylcellulose phthalate, hydroxypropyl methylcellulose acetate succinate, polyvinyl alcohol phthalate, shellac, hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, ethyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, pullulan, collagen, casein, agar, gum arabic, sodium carboxymethyl cellulose, (swellable hydrophilic polymers) poly(hydroxyalkyl methacrylate) (molecular weight 5 k to 5000 k), polyvinylpyrrolidone (molecular weight 10 k to 360 k), anionic and cationic hydrogels, zein, polyamides, polyvinyl alcohol having a low acetate residual, a swellable mixture of agar and carboxymethyl cellulose, copolymers of maleic anhydride and styrene, ethylene, propylene or isobutylene, pectin (molecular weight 30 k to 300 k), polysaccharides such as agar, acacia, karaya, tragacanth, algins and guar, polyacrylamides, POLYOX® polyethylene oxides (molecular weight 100 k to 5000 k, Dow), AQUA KEEP® acrylate polymers (composed of mainly acrylic acid polymer, sodium salt), diesters of polyglucan, crosslinked polyvinyl alcohol and poly N-vinyl-2-pyrrolidone, hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, methyl ethyl cellulose, ethylhydroxy ethylcellulose, cellulose acetate, cellulose butyrate, cellulose propionate, gelatin, starch, maltodextrin, pullulan, polyvinyl pyrrolidone, polyvinyl alcohol, polyvinyl acetate, glycerol fatty acid esters, polyacrylamide, polyacrylic acid, natural gums, lecithins, pectin, alginates, ammonia alginate, sodium, calcium, potassium alginates, propylene glycol alginate, agar, and gums such as arabic, karaya, locust bean, tragacanth, carrageenan, guar, xanthan, scleroglucan and mixtures and blends thereof.

In some embodiments, the dosage forms of reboxetine (including S,S-reboxetine) are coated with polymers in order to facilitate mucoadhesion within the gastrointestinal tract. Non-limiting examples of polymers that can be used for mucoadhesion include carboxymethylcellulose, polyacrylic acid, Carbopol™ (Lubrizol), polycarbophil, gelatin and other natural or synthetic polymers.

The polymeric coatings of the present disclosure may be any one of the described coatings or may be a combination of two or more of the described coatings to achieve the desired release profiles of the release of reboxetine (including S,S-reboxetine).

In addition to the modified release dosage forms described herein, other modified release technologies known to those skilled in the art can be used in order to achieve the modified release formulations of the present disclosure, i.e., formulations which provide a mean $T_{max}$ of the drug and/or other pharmacokinetic parameters described herein when administered e.g., orally or by other mode of administration to human patients. Such formulations can be manufactured as a modified release oral formulation in a suitable tablet or multiparticulate formulation known to those skilled in the art. In either case, the modified release dosage form can optionally include a controlled release carrier which is incorporated into a matrix along with the drug, or which is applied as a controlled release coating. Any dosage form comprising an effective amount of reboxetine (including S,S-reboxetine) may further comprise a binder, a lubricant, and other conventional inert excipients.

A binder (also sometimes called adhesive) can be added to a drug-filler mixture to increase the mechanical strength of the granules and tablets during formation. Binders can be added to the formulation in different ways: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction. In this form the binder is referred to as a dry binder. Solution binders are a common way of incorporating a binder into granules. In certain embodiments, the binder used in the tablets is in the form of a solution binder. Non-limiting examples of binders useful include hydrogenated vegetable oil, castor oil, paraffin, higher aliphatic alcohols, higher aliphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Specific examples of water-soluble polymer binders include modified starch, gelatin, polyvinylpyrrolidone, cellulose derivatives (e.g., hydroxypropyl methylcellulose (HPMC) and hydroxypropyl cellulose (HPC)), polyvinyl alcohol and mixtures thereof. Any suitable amount of binder may be present, such as about 0.5-5%, about 5-10%, about 10-15%, about 15-20%, about 20-25%, about 0.5-25%, about 0.5-15%, about 1-6%, or about 3% by weight of the tablet dry weight. In some embodiments, the binder is polyvinyl alcohol.

Lubricants can be added to pharmaceutical formulations to decrease any friction that occurs between the solid and the die wall during tablet manufacturing. High friction during tableting can cause a series of problems, including inadequate tablet quality (capping or even fragmentation of tablets during ejection, and vertical scratches on tablet edges) and may even stop production. Accordingly, lubricants may be added to tablet formulations. Non-limiting examples of lubricants useful include glyceryl behenate, stearic acid, hydrogenated vegetable oils (such as hydrogenated cottonseed oil (STEROTEX®), hydrogenated soybean oil (STEROTEX® HM) and hydrogenated soybean oil & castor wax (STEROTEX® K), stearyl alcohol, leucine, polyethylene glycol (MW 1450, suitably 4000, and higher), magnesium stearate, glyceryl monostearate, stearic acid, polyethylene glycol, ethylene oxide polymers (for example, available under the registered trademark CARBOWAX® from Union Carbide, Inc., Danbury, Conn.), sodium lauryl sulfate, magnesium lauryl sulfate, sodium oleate, sodium stearyl fumarate, DL-leucine, colloidal silica, mixtures thereof and others as known in the art. In some embodiments, the lubricant is glyceryl behenate (for example, COMPRITOL® 888). Any suitable amount of binder may be present, such as about 0.5-5%, about 5-10%, about 10-15%, about 15-20%, about 20-25%, about 0.5-25%, about 0.5-15%, about 1-6%, or about 3% by weight of the tablet dry weight.

In some embodiments, reboxetine (including S,S-reboxetine) is administered once a day or twice a day for at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 4 months, at least about 5 months, at least about 6 months, at least about 7 months, at least about 8 months, at least about 9 months, at least about 10 months, at least about 11 months, at least about 12 months, at least 1.5 years, at least 2 years, at least about 3 years, at least about 4 years, at least about 5 years, about 0.1-5 years, about 5-10 years, at least about 10 years, about 10-15 years, at least about 15 years, about 15-20 years, at least about 20 years, or longer. In some embodiments, reboxetine (including S,S-reboxetine) is administered for up to about 6 months, up to about 1 year, up to about 2 years, up to about 5 years, up to about 10 years, up to about 20 years, up to about 40 years, up to about 60 years, or up to about 90 years.

An example, not as an attempt to limit the scope of the disclosure, of a useful composition for a dosage form containing about 5-10 mg of reboxetine (including S,S-reboxetine) is shown in Table 1 below:

TABLE 1

Example of dosage form of reboxetine

| Component | Amount (wt/wt) |
| --- | --- |
| Reboxetine or S,S-reboxetine | 30-70% |
| lubricant | 1-10% |
| diluent | 20-70% |
| disintegrant | 1-10% |

Treatment of narcolepsy with cataplexy with reboxetine (including S,S-reboxetine) in the dosage forms described herein may not have significant side effects as the existing treatment options. Treatment of narcolepsy with cataplexy with reboxetine (including S,S-reboxetine) in the dosage forms described herein may be well tolerated in mammals such as human beings.

Some embodiments include a kit comprising a pharmaceutical composition comprising one or more units of a dosage form (e.g., about 1-30, about 30-60, about 60-90, about 90-120, about 120-180, about 180-360, or about 360-720 units of a dosage form), wherein a unit of the dosage form comprises about 0.1-5 mg of reboxetine (including S,S-reboxetine) and instructions to use the pharmaceutical composition to treat narcolepsy with cataplexy in a human being.

Some embodiments include a kit comprising a pharmaceutical composition comprising one or more units of a dosage form (e.g., about 1-30, about 30-60, about 60-90, about 90-120, about 120-180, about 180-360, or about 360-720 units of a dosage form), wherein a unit of the dosage form comprises about 5-10 mg of reboxetine (including S,S-reboxetine) and instructions to use the pharmaceutical composition to treat narcolepsy with cataplexy in a human being.

Some embodiments include a kit comprising a pharmaceutical composition comprising one or more units of a dosage form (e.g., about 1-30, about 30-60, about 60-90, about 90-120, about 120-180, about 180-360, or about 360-720 units of a dosage form), wherein a unit of the dosage form comprises about 10-15 mg of reboxetine (including S,S-reboxetine) and instructions to use the pharmaceutical composition to treat narcolepsy with cataplexy in a human being.

Some embodiments include a kit comprising a pharmaceutical composition comprising one or more units of a dosage form (e.g., about 1-30, about 30-60, about 60-90, about 90-120, about 120-180, about 180-360, or about 360-720 units of a dosage form), wherein a unit of the dosage form comprises about 15-20 mg of reboxetine (including S,S-reboxetine) and instructions to use the pharmaceutical composition to treat narcolepsy with cataplexy in a human being.

Some embodiments include a kit comprising a pharmaceutical composition comprising one or more units of a dosage form (e.g., about 1-30, about 30-60, about 60-90, about 90-120, about 120-180, about 180-360, or about 360-720 units of a dosage form), wherein a unit of the dosage form comprises about 5-20 mg of reboxetine (including S,S-reboxetine) and instructions to use the pharmaceutical composition to treat narcolepsy with cataplexy in a human being.

The following embodiments are specifically contemplated.

Embodiment 1. A method of treating narcolepsy with cataplexy, comprising administering reboxetine to a human being in need thereof, wherein reboxetine is administered at least once daily for more than two weeks, wherein, two weeks from the beginning of treatment, the human being experiences a reduction in the number of cataplexy attacks in a week, a reduction in the Epworth Sleepiness Scale score, a decrease in the cataplexy subscore on the Ullanlinna Narcolepsy Scale (NUS), or a reduction in the Maintenance of Wakefulness Test score as a result of the treatment.

Embodiment 2. Use of reboxetine in the manufacture of a medicament for the treatment of narcolepsy with cataplexy, wherein reboxetine is administered at least once daily for at least three weeks.

Embodiment 3. A kit comprising a pharmaceutical composition comprising reboxetine and instructions to use the pharmaceutical composition to treat narcolepsy with cataplexy in a human being, wherein reboxetine is administered at least once daily for at least three weeks.

Embodiment 4. The method, the use, or the kit of embodiment 1, 2, or 3, wherein reboxetine is administered twice daily, wherein a first dosage form is administered in the morning and a second dosage form is administered about 2 hours to about 6 hours later.

Embodiment 5. The method, the use, or the kit of embodiment 4, wherein the second dosage form is administered about 2 hours to about 3 hours after the first dosage form.

Embodiment 6. The method, the use, or the kit of embodiment 4, wherein the second dose is administered about 3 hours to about 4 hours after the first dosage form.

Embodiment 7. The method, the use, or the kit of embodiment 4, wherein the second dosage form is administered about 4 hours to about 5 hours after the first dosage form.
Embodiment 8. The method, the use, or the kit of embodiment 4, wherein the second dosage form is administered about 5 hours to about 6 hours after the first dosage form.
Embodiment 9. The method, the use, or the kit of embodiment 1, wherein a single dosage form is administered daily, wherein the single dosage form contains a first release component comprising reboxetine and a second release component comprising reboxetine, wherein the first release component provides a first local maximum in the plasma concentration of reboxetine and the second release component provides a second local maximum in the plasma concentration of reboxetine, wherein the first local maximum in the plasma concentration of reboxetine occurs about 2 to about 6 hours before the second local maximum in the plasma concentration of reboxetine.
Embodiment 10. The method, the use, or the kit of embodiment 9, wherein the second local maximum in the plasma concentration of reboxetine occurs about 2 to about 3 hours after the first local maximum in the plasma concentration of reboxetine.
Embodiment 11. The method, the use, or the kit of embodiment 9, wherein the second local maximum in the plasma concentration of reboxetine occurs about 3 to about 4 hours after the first local maximum in the plasma concentration of reboxetine.
Embodiment 12. The method, the use, or the kit of embodiment 9, wherein the second local maximum in the plasma concentration of reboxetine occurs about 4 to about 5 hours after the first local maximum in the plasma concentration of reboxetine.
Embodiment 13. The method, the use, or the kit of embodiment 9, wherein the second local maximum in the plasma concentration of reboxetine occurs about 5 to about 6 hours after the first local maximum in the plasma concentration of reboxetine.
Embodiment 14. The method, the use, or the kit of embodiment 1, 2, 3, 4, 5, 6, 7, 8, 9, 10, or 11, 12, or 13, wherein the human being is selected for not suffering from depression.
Embodiment 15. The method, the use, or the kit of embodiment 1, 2, 3, 4, 5, 6, 7, 8, 9, 10, 11, 12, 13, or 14, the dose amount of reboxetine is increased for 1 to 7 days, and then maintained constant at a total daily dose of about 0.006 mmol to about 0.01 mmol.
Embodiment 16. The method, the use, or the kit of embodiment 1, 2, 3, 4, 5, 6, 7, 8, 9, 10, 11, 12, 13, 14, or 15, wherein the dose amount of reboxetine is increased for 1 to 7 days, and then maintained constant at a total daily dose of about 0.01 mmol to about 0.02 mmol.
Embodiment 17. The method, the use, or the kit of embodiment 1, 2, 3, 4, 5, 6, 7, 8, 9, 10, 11, 12, 13, 14, or 15, wherein the dose of reboxetine is increased for 1 to 7 days, and then maintained constant at a total daily dose of about 0.02 mmol to about 0.03 mmol.
Embodiment 18. The method, the use, or the kit of embodiment 1, 2, 3, 4, 5, 6, 7, 8, 9, 10, 11, 12, 13, 14, or 15, wherein the dose of reboxetine is increased for 1 to 7 days, and then maintained constant at a total daily dose of about 0.03 mmol to about 0.04 mmol.
Embodiment 19. The method, the use, or the kit of embodiment 1, 2, 3, 4, 5, 6, 7, 8, 9, 10, 11, 12, 13, 14, or 15, wherein the dose of reboxetine is increased for 1 to 7 days, and then maintained constant at a total daily dose of about 0.04 mmol to about 0.05 mmol.
Embodiment 20. The method, the use, or the kit of embodiment 1, 2, 3, 4, 5, 6, 7, 8, 9, 10, 11, 12, 13, 14, or 15, wherein the dose of reboxetine is increased for 1 to 7 days, and then maintained constant at a total daily dose of about 0.05 mmol to about 0.06 mmol.
Embodiment 21. The method, the use, or the kit of embodiment 1, 2, 3, 4, 5, 6, 7, 8, 9, 10, 11, 12, 13, 14, or 15, wherein the dose of reboxetine is increased for 1 to 7 days, and then maintained constant at a total daily dose of about 0.06 mmol to about 0.07 mmol.
Embodiment 22. The method, the use, or the kit of embodiment 1, 2, 3, 4, 5, 6, 7, 8, 9, 10, 11, 12, 13, 14, or 15, wherein the dose of reboxetine is increased for 1 to 7 days, and then maintained constant at a total daily dose of about 0.07 mmol to about 0.08 mmol.
Embodiment 23. The method, the use, or the kit of embodiment 1, 2, 3, 4, 5, 6, 7, 8, 9, 10, 11, 12, 13, 14, 15, 16, 17, 18, 19, 20, 21, or 22, wherein the reboxetine is in a dosage form and the dosage form contains about 5 mg of reboxetine.
Embodiment 24. The method, the use, or the kit of embodiment 1, 2, 3, 4, 5, 6, 7, 8, 9, 10, 11, 12, 13, 14, 15, 16, 17, 18, 19, 20, 21, or 22, wherein the reboxetine is in a dosage form and the dosage form contains about 10 mg of reboxetine.
Embodiment 25. The method, the use, or the kit of embodiment 23, wherein the dosage form is administered once daily or twice daily for at least three weeks.
Embodiment 26. The method, the use, or the kit of embodiment 24, wherein the dosage form is administered once daily or twice daily for at least three weeks.
Embodiment 27. The method, the use, or the kit of embodiment 1, 2, 3, 4, 5, 6, 7, 8, 9, 10, 11, 12, 13, 14, 15, 16, 17, 18, 19, 20, 21, 22, 23, 24, 25, or 26, wherein the human being experiences an increase in sleep latency on the multiple sleep latency test (MSLT).
Embodiment 28. The method, the use, or the kit of embodiment 27, wherein the human being experiences an increase of at least 10% in sleep latency on the MSLT.
Embodiment 29. The method, the use, or the kit of embodiment 27, wherein the human being experiences an increase of at least 20% in sleep latency on the MSLT.
Embodiment 30. The method, the use, or the kit of embodiment 27, wherein the human being experiences an increase of at least 30% in sleep latency on the MSLT.
Embodiment 31. The method, the use, or the kit of embodiment 27, wherein the human being experiences an increase of at least 40% in sleep latency on the MSLT.
Embodiment 32. The method, the use, or the kit of embodiment 27, wherein the human being experiences an increase of at least 50% in sleep latency on the MSLT.
Embodiment 33. The method, the use, or the kit of embodiment 27, wherein the human being experiences an increase of at least 60% in sleep latency on the MSLT.
Embodiment 34. The method, the use, or the kit of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33, wherein the human being experiences a decrease of at least 15% in the cataplexy subscore on the UNS.
Embodiment 35. The method, the use, or the kit of embodiment 34, wherein the human being experiences a decrease of at least 20% in the cataplexy subscore on the UNS.
Embodiment 36. The method, the use, or the kit of embodiment 34, wherein the human being experiences a decrease of at least 30% in the cataplexy subscore on the UNS.
Embodiment 37. The method, the use, or the kit of embodiment 34, wherein the human being experiences a decrease of at least 40% in the cataplexy subscore on the UNS.

Embodiment 38. The method, the use, or the kit of embodiment 34, wherein the human being experiences a decrease of at least 50% in the cataplexy subscore on the UNS.

Embodiment 39. The method, the use, or the kit of embodiment 34, wherein the human being experiences a decrease of at least 60% in the cataplexy subscore on the UNS.

Embodiment 40. The method, the use, or the kit of embodiment 34, wherein the human being experiences a decrease of at least 70% in the cataplexy subscore on the UNS.

Embodiment 41. The method, the use, or the kit of embodiment 34, wherein the human being has a cataplexy subscore of about 0.

Embodiment 42. A method of improving the ability to concentrate in a human being suffering from narcolepsy, comprising administering reboxetine to a human being in need thereof.

Embodiment 43. The method of embodiment 42, wherein the human being is selected for being in need of improvement in ability to concentrate or for having difficulty concentrating.

Embodiment 44. The method of embodiment 42 or 43, wherein, as compared to before any reboxetine is administered, the human being has an improvement in the Ability to Concentrate item of the NSAQ that is at least about –0.1.

Embodiment 45. A method of treating fibromyalgia, comprising administering esreboxetine to a human being in need thereof, wherein a daily dose of about 1 mg to about 2 mg of esreboxetine is administered for at least six weeks, wherein the human being experiences a reduction in fibromyalgia pain during the course of the treatment, as measured by a visual analog scale (VAS) score, that is greater than the reduction in pain that the human being would have experienced by administering a placebo.

Embodiment 46. The method of embodiment 45, wherein about 1 mg to about 2 mg of esreboxetine is administered once a day.

Embodiment 47. The method of embodiment 45, wherein about 0.5 mg to about 1 mg of esreboxetine is administered twice a day.

Embodiment 48. The method of embodiment 45, 46, or 47, wherein the human being is selected for having a Global Fatigue Index score of at least about 8.

Embodiment 49. The method of embodiment 45, 46, 47, or 48, wherein after esreboxetine is administered daily for six weeks, the VAS score of the fibromyalgia pain of the human being is reduced by at least 20% as compared to the VAS score of the fibromyalgia pain of the human being immediately prior to administering the first dose of esreboxetine.

Embodiment 50. The method of embodiment 45, 46, 47, 48, or 49, wherein after esreboxetine is administered daily for six weeks, the VAS score of the fibromyalgia pain of the human being is reduced by at least 50% as compared to the VAS score of the fibromyalgia pain of the human being immediately prior to administering the first dose of esreboxetine.

Embodiment 51. A method of treating fibromyalgia, comprising administering esreboxetine to a human being in need thereof, wherein a daily dose of about 2 mg to about 4 mg of esreboxetine is administered for at least six weeks, wherein the human being experiences a reduction in pain during the course of the treatment, as measured by a visual analog scale (VAS) score, that is greater than the reduction in pain that the human being would have experienced by administering a placebo.

Embodiment 52. The method of embodiment 51, wherein about 1 mg to about 2 mg of esreboxetine is administered once a day.

Embodiment 53. The method of embodiment 51, wherein about 0.5 mg to about 1 mg of esreboxetine is administered twice a day.

Embodiment 54. The method of embodiment 51, 52, or 53, wherein the human being is selected for having a Global Fatigue Index score of at least about 8.

Embodiment 55. The method of embodiment 51, 52, 53, or 54, wherein after esreboxetine is administered daily for six weeks, the VAS score of the fibromyalgia pain of the human being is reduced by at least 20% as compared to the VAS score of the fibromyalgia pain of the human being immediately prior to administering the first dose of esreboxetine.

Embodiment 56. The method of embodiment 51, 52, 53, 54, or 55, wherein after esreboxetine is administered daily for six weeks, the VAS score of the fibromyalgia pain of the human being is reduced by at least 50% as compared to the VAS score of the fibromyalgia pain of the human being immediately prior to administering the first dose of esreboxetine.

Embodiment 57. A method of treating fibromyalgia, comprising administering esreboxetine to a human being in need thereof, wherein a daily dose of about 0.5 mg to about 1 mg of esreboxetine is administered for at least six weeks, wherein the human being experiences a reduction in pain during the course of the treatment, as measured by a visual analog scale (VAS) score, that is greater than the reduction in pain that the human being would have experienced by administering a placebo.

Embodiment 58. The method of embodiment 57, wherein about 1 mg to about 2 mg of esreboxetine is administered once a day.

Embodiment 59. The method of embodiment 57, wherein about 0.5 mg to about 1 mg of esreboxetine is administered twice a day.

Embodiment 60. The method of embodiment 57, 58, or 59, wherein the human being is selected for having a Global Fatigue Index score of at least about 8.

Embodiment 61. The method of embodiment 57, 58, 59, or 60, wherein after esreboxetine is administered daily for six weeks, the VAS score of the fibromyalgia pain of the human being is reduced by at least 20% as compared to the VAS score of the fibromyalgia pain of the human being immediately prior to administering the first dose of esreboxetine.

Embodiment 62. The method of embodiment 61, wherein after esreboxetine is administered daily for six weeks, the VAS score of the fibromyalgia pain of the human being is reduced by at least 50% as compared to the VAS score of the fibromyalgia pain of the human being immediately prior to administering the first dose of esreboxetine.

EXAMPLES

Example 1

A 40 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After one week of treatment, the number of cataplexy attacks have decreased by 10-30%.

Example 2

A 20 year old female is diagnosed as suffering from narcolepsy with cataplexy. She is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After one week of treatment, the number of cataplexy attacks have decreased by 30-60%.

Example 3

A 60 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After one week of treatment, the number of cataplexy attacks have decreased by 60-100%.

Example 4

A 50 year old female is diagnosed as suffering from narcolepsy with cataplexy. She is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After one week of treatment, the ESS score has decreased by 10-30%.

Example 5

A 25 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After one week of treatment, the ESS score has decreased by 30-60%.

Example 6

A 47 year old female is diagnosed as suffering from narcolepsy with cataplexy. She is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After one week of treatment, the ESS score has decreased by 60-100%.

Example 7

A 19 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After one week of treatment, the MWT score has decreased by 10-30%.

Example 8

A 42 year old female is diagnosed as suffering from narcolepsy with cataplexy. She is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After one week of treatment, the MWT score has decreased by 30-60%.

Example 9

A 33 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After one week of treatment, the MWT score has decreased by 60-100%.

Example 10

A 54 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the number of cataplexy attacks have decreased by 10-30%.

Example 11

A 27 year old female is diagnosed as suffering from narcolepsy with cataplexy. She is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the number of cataplexy attacks have decreased by 30-60%.

Example 12

A 52 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the number of cataplexy attacks have decreased by 60-100%.

Example 13

A 66 year old female is diagnosed as suffering from narcolepsy with cataplexy. She is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the ESS score has decreased by 10-30%.

Example 14

A 34 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the ESS score has decreased by 30-60%.

Example 15

A 35 year old female is diagnosed as suffering from narcolepsy with cataplexy. She is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the ESS score has decreased by 60-100%.

Example 16

A 19 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the MWT score has decreased by 10-30%.

Example 17

A 70 year old female is diagnosed as suffering from narcolepsy with cataplexy. She is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the MWT score has decreased by 30-60%.

Example 18

A 57 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the MWT score has decreased by 60-100%.

Example 19

A 20 year old female is diagnosed as suffering from narcolepsy with cataplexy. She is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the HAM-D score has decreased by 10-30%.

Example 20

A 69 year old male is diagnosed as suffering from narcolepsy with cataplexy. He is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the HAM-D score has decreased by 30-60%.

Example 21

A 56 year old female is diagnosed as suffering from narcolepsy with cataplexy. She is given reboxetine and instructed to take 5 mg of reboxetine at 8 am and 5 mg of reboxetine at 1 pm for three weeks. The patient is evaluated prior to treatment, and weekly to determine the MWT score, the number of cataplexy attacks, the PGI-C score, the HAM-D score, the ESS score, the NSAQ score, and the ability to concentrate on the NSAQ. After three weeks of treatment, the HAM-D score has decreased by 60-100%.

Example 22

A Phase 2, double-blind, randomized, placebo-controlled, crossover, multicenter trial of reboxetine was carried out in patients with narcolepsy. A total of 21 patients with a diagnosis of narcolepsy with cataplexy were treated for 2 weeks with reboxetine or with placebo, followed by a crossover to the other treatment after a 1-week down-titration and washout period. Reboxetine was administered orally twice daily, with a total daily dose of 8 mg for Week 1 which was escalated to 10 mg for Week 2. Patients were randomized in a 1:1 ratio either to treatment with reboxetine followed by placebo (sequence 1), or to treatment with placebo followed by reboxetine (sequence 2). The average number of cataplexy attacks at baseline was 30. Key assessments were made daily using an electronic diary. The prespecified primary endpoint was the change in the weekly number of cataplexy attacks, averaged over the 2-week treatment period (overall treatment effect). Secondary endpoints included changes in the number of inadvertent naps, cognition, and Epworth Sleepiness Scale. Cognition was assessed using the Ability to Concentrate item of the Narcolepsy Symptom Assessment Questionnaire, a patient reported outcome measure. This item is rated on 5-point scale (1=very good to 5=very poor). All analyses were conducted on an intent-to-treat basis.

Figure 2:
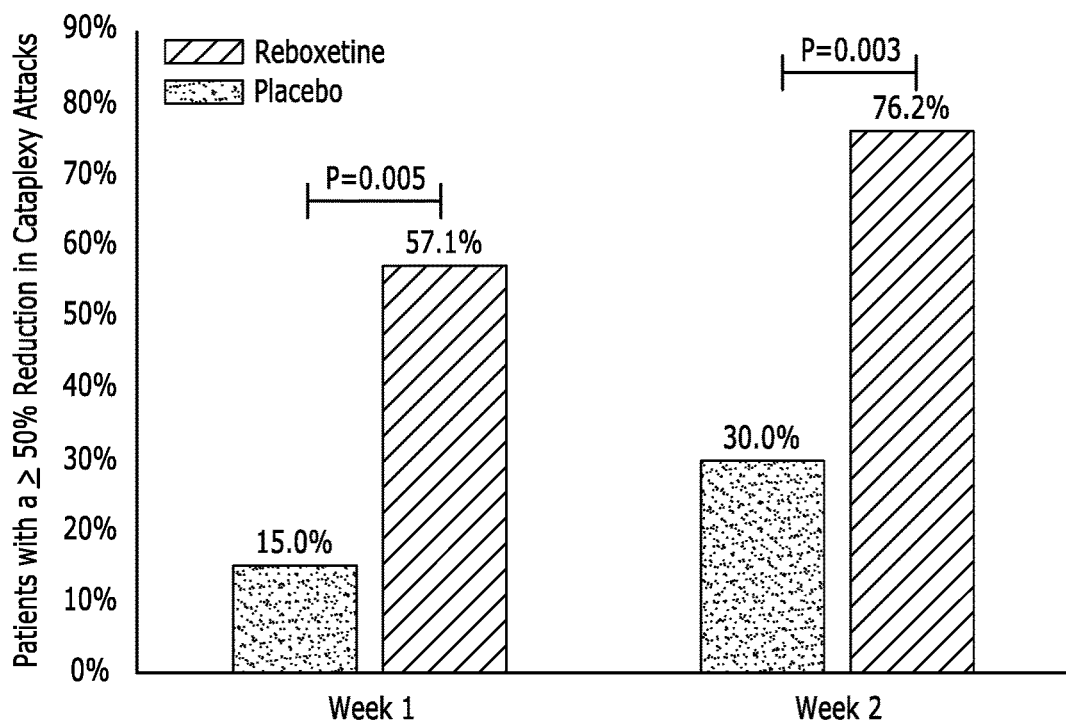
FIG. 2 depicts the number of human patients with a 50% or greater reduction in weekly cataplexy attacks, where the human patients received reboxetine or placebo as described in Example 22.
Figure 3:
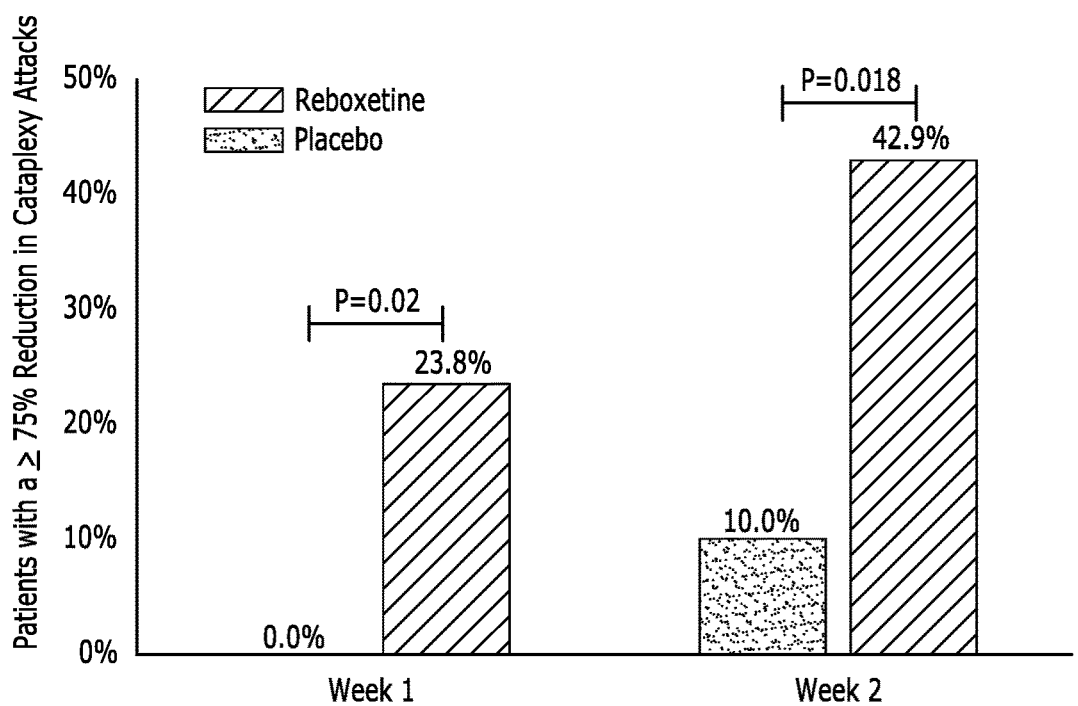
FIG. 3 depicts the number of human patients with a 75% or greater reduction in weekly cataplexy attacks, where the human patients received reboxetine or placebo as described in Example 22.

As shown in FIG. 1, Reboxetine met the prespecified primary endpoint by demonstrating a highly statistically significant reduction from baseline in the mean weekly number of cataplexy attacks, averaged for the 2-week treatment period (overall treatment effect), as compared to placebo (p<0.001). At Week 2, reboxetine demonstrated a mean reduction of 14.6 cataplexy attacks per week compared to a reduction of 2.6 attacks per week for placebo (p=0.002), representing mean reductions of 48.7% and 8.7% from baseline, respectively (FIG. 1). Furthermore, Reboxetine treatment resulted in rapid reduction in the cataplexy attacks. After 1-week treatment, reboxetine demonstrated a mean reduction of 13.0 cataplexy attacks compared to a reduction of 0.3 attacks for placebo (p<0.001), representing mean reductions of 43.3% and 1.0% from baseline, respectively (FIG. 1). The proportion of patients achieving a 50% or greater reduction in the weekly number of cataplexy attacks was 76.2% for reboxetine, compared to 30.0% for placebo (p=0.003) at Week 2 (FIG. 2). The proportion of patients achieving a 75% or greater reduction in the weekly number of cataplexy attacks was 42.9% for reboxetine, compared to 10.0% for placebo (p=0.018) at Week 2 (FIG. 3). The improvement in cataplexy was rapid with reboxetine demonstrating significant benefit over placebo as early as Week 1 (p<0.001).

Figure 4:
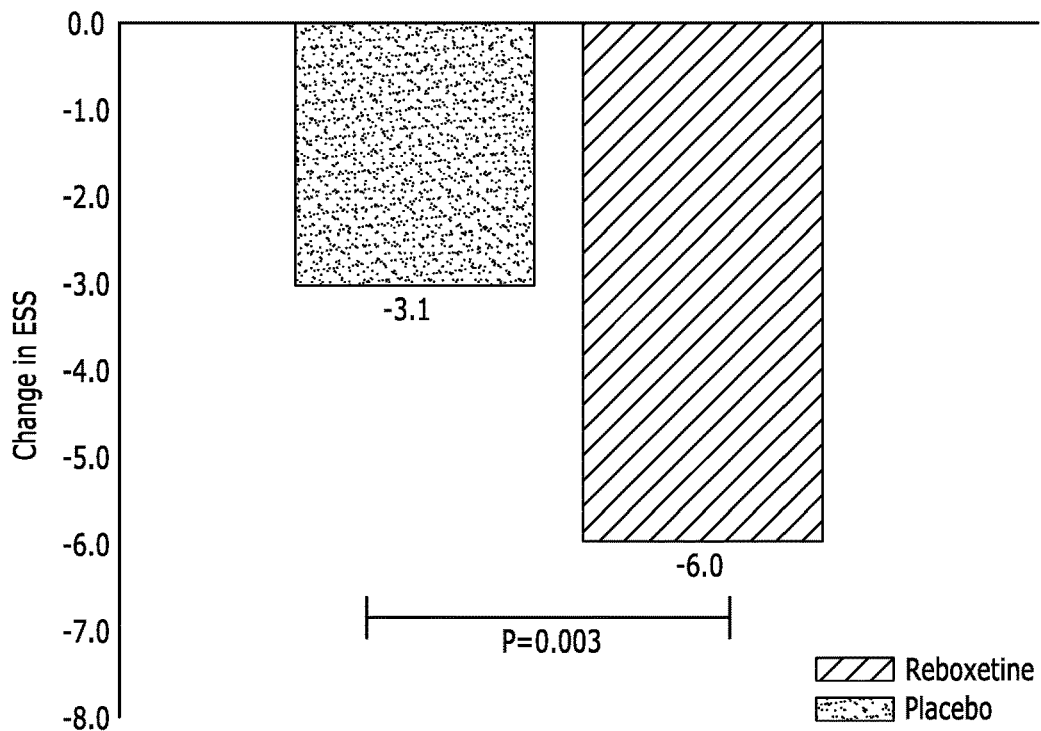
FIG. 4 depicts the change in Epworth Sleepiness Scale Score for human patients who received reboxetine or placebo as described in Example 22.
Figure 5:
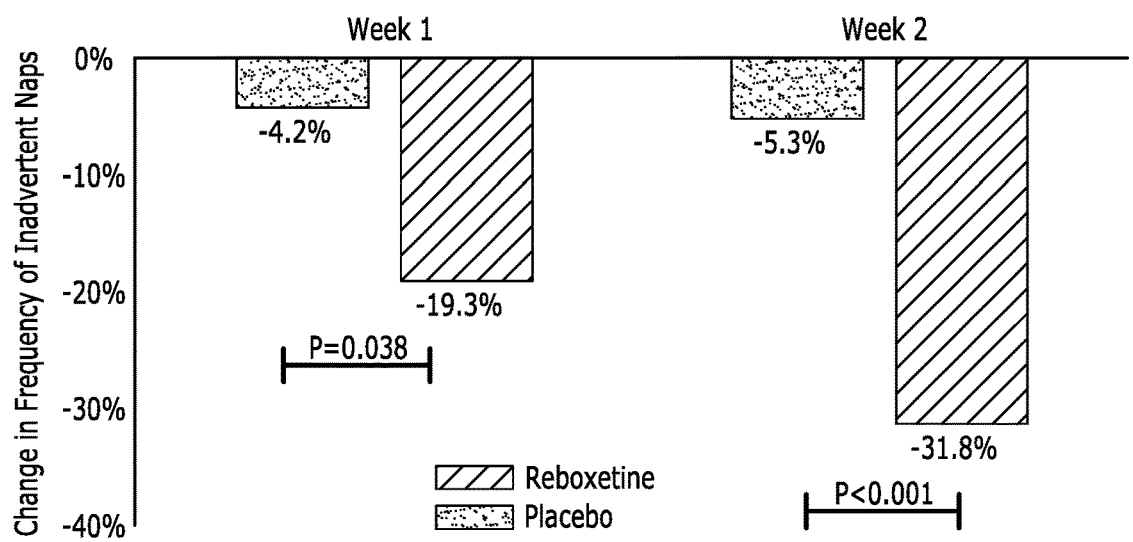
FIG. 5 depicts the reduction in the weekly frequency of inadvertent naps for human patients who received reboxetine or placebo as described in Example 22.
Figure 6:
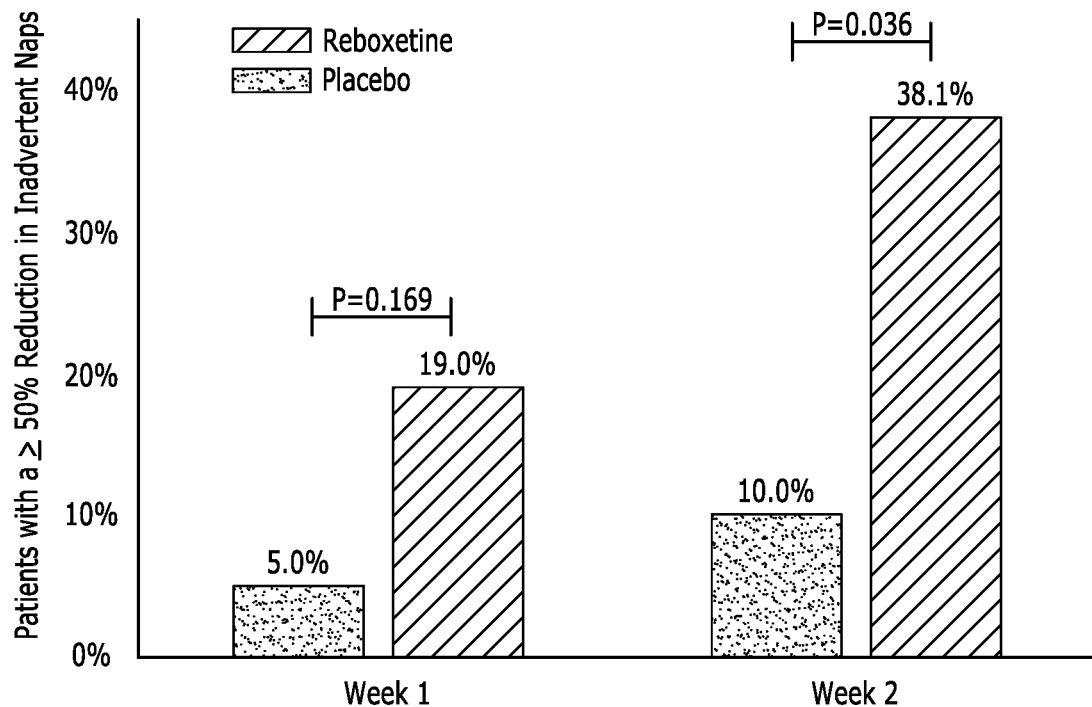
FIG. 6 depicts the number of human patients with a 50% or greater reduction in inadvertent naps, where the human patients received reboxetine or placebo as described in Example 22.

Reboxetine significantly improved EDS (excessive daytime sleepiness) symptoms compared to placebo, as measured by the Epworth Sleepiness Scale (ESS) and by the frequency of inadvertent naps. As shown in FIG. 4, the improvement on the ESS with reboxetine treatment was twice that observed with placebo, with reductions in the ESS score from baseline of 6.0 and 3.1, respectively for reboxetine and placebo (p=0.003). Reboxetine treatment resulted in a 31.8% mean reduction from baseline in the average weekly number of inadvertent naps versus a 5.3% mean reduction for placebo (p<0.001) at Week 2 (FIG. 5). As shown in FIG. 6, reboxetine treatment resulted in a greater number of patients with 50% or greater reduction in inadvertent naps (38.1%) as compared to placebo (10.0%) (p=0.036). The improvement in frequency of inadvertent naps was rapid with reboxetine demonstrating significant benefit over placebo as early as Week 1.

Figure 7:
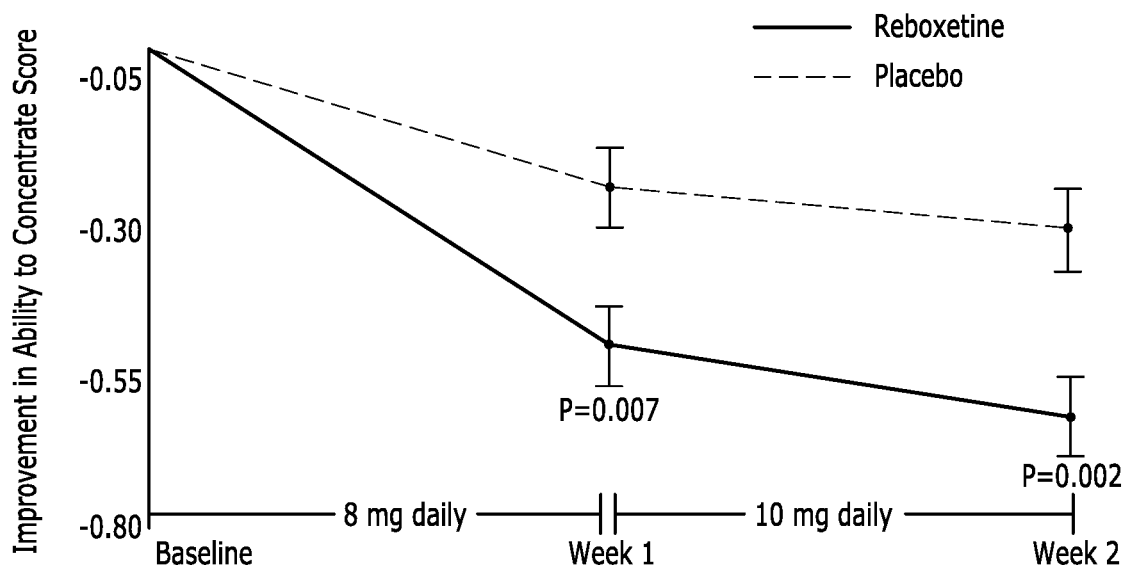
FIG. 7 depicts the improvement in the ability to concentrate score for human patients who received reboxetine or placebo as described in Example 22.
Figure 8:
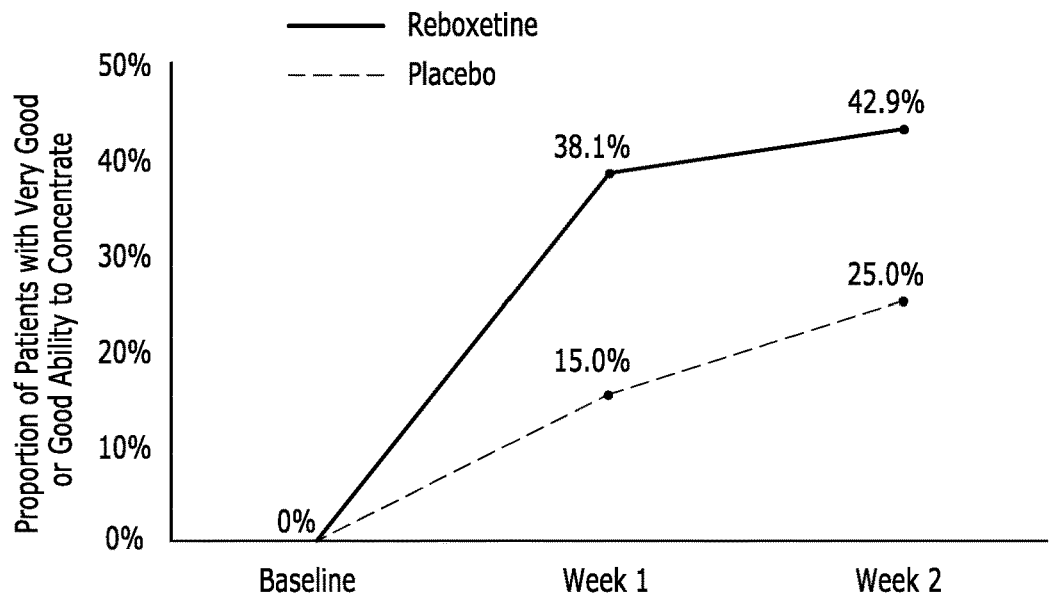
FIG. 8 depicts the number of human patients with a "very good" or "good" ability to concentrate, where the human patients received reboxetine or placebo as described in Example 22.

Reboxetine significantly improved cognitive function compared to placebo over the 2-week treatment period as measured by the Ability to Concentrate item of the Narcolepsy Symptom Assessment Questionnaire (NSAQ), which was assessed daily (p<0.01) (FIGS. 7-8). For this assessment, patients rated their ability to concentrate on a 5-point scale (1=very good, 2=good, 3=average, 4=poor, and 5=very poor). At the end of the 2-week treatment period, 42.9% of patients had an ability to concentrate that was "good" to "very good" with reboxetine treatment, compared to 25.0% of patients with placebo, and 0% of patients at baseline. The improvement in the ability to concentrate was rapid with reboxetine demonstrating significant improvement over placebo (38.1% vs 15.0%) as early as Week 1 (p=0.007).

Figure 9:
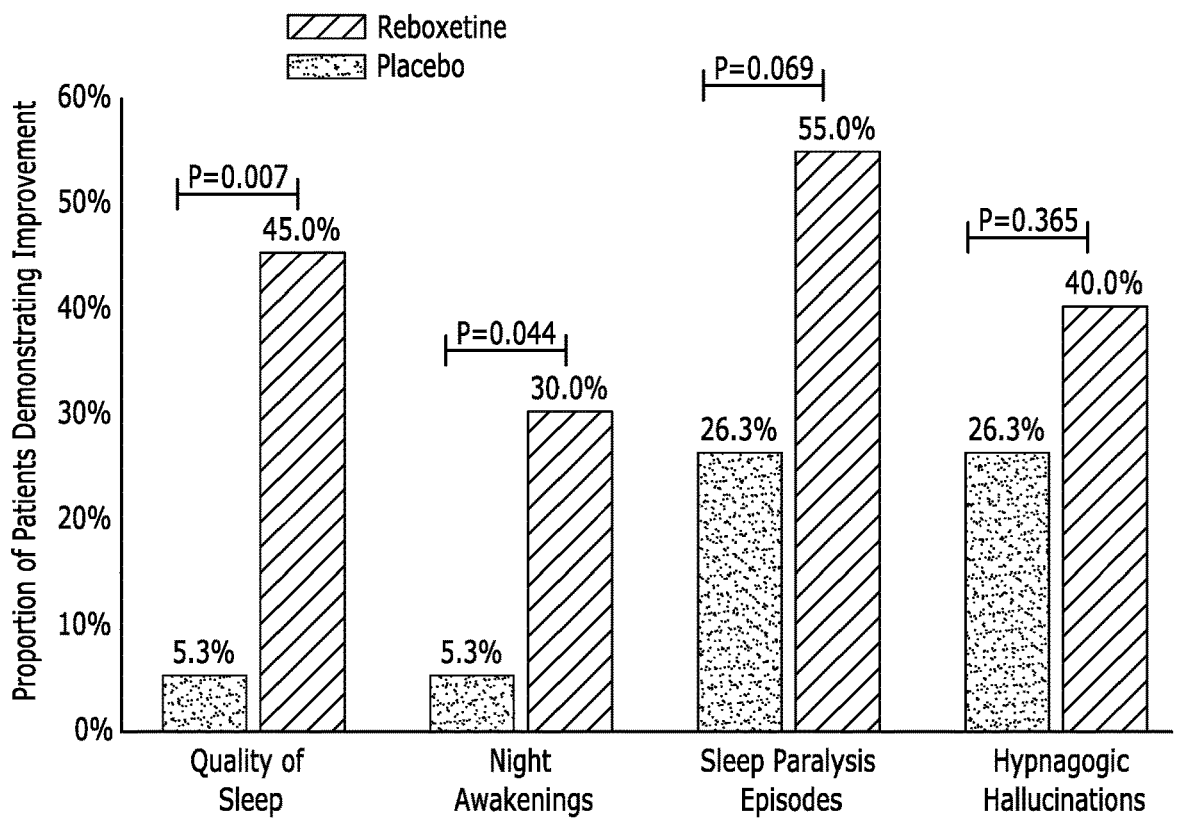
FIG. 9 depicts the proportion of human patients demonstrating improvement in sleep quality, night awakenings, sleep paralysis episodes, and hypnagogic hallucinations.

Reboxetine significantly improved sleep quality, as measured by overall improvement and by number of awakenings at night, and reduced sleep-related symptoms, as compared to placebo. As shown in FIG. 9, reboxetine treatment resulted in 45.0% of patients reporting improved sleep quality versus 5.3% of patients with placebo (p=0.007). Reboxetine treatment resulted in 30.0% of patients reporting a reduction in the number of awakenings at night versus 5.3% of patients with placebo (p=0.044). Reboxetine treatment also resulted in greater proportion of patients with reductions in sleep paralysis episodes, and in hypnagogic hallucinations, as compared to placebo.

Reboxetine was safe and well tolerated. There were no serious adverse events reported in the trial, and no discontinuations due to adverse events. The overall percentage of patients experiencing adverse events was 42.9% with reboxetine and 40.0% with placebo, with the most commonly reported adverse events with reboxetine treatment being anxiety, constipation, and insomnia. The completion rate was 91% for patients randomized to treatment sequence 1 (reboxetine followed by placebo) and 100% for those randomized to sequence 2 (placebo followed by reboxetine).

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A method of reducing daytime sleepiness, comprising administering 8 mg to 10 mg of reboxetine daily for at least two weeks to a human being in need thereof, wherein the human being is experiencing narcolepsy with cataplexy, wherein during the second week that reboxetine is administered, the human being experiences less daytime sleepiness than the week before the human being first received reboxetine, as determined by the human being's Epworth Sleepiness Scale scores.

2. The method of claim 1, wherein the human being is selected for having experienced at least 7 cataplexy attacks in the week before the human being first received reboxetine.

3. The method of claim 1, wherein reboxetine is administered once a day.

4. The method of claim 1, wherein reboxetine is administered in a dosage form further containing a polymer.

5. The method of claim 1, wherein reboxetine is administered in a dosage form further containing a binder.

6. The method of claim 1, wherein reboxetine is administered in a dosage form further containing a lubricant.

7. The method of claim 1, wherein reboxetine is administered in a dosage form further containing a diluent.

8. The method of claim 1, wherein reboxetine is administered in a dosage form further containing a disintegrant.

9. The method of claim 1, wherein 4 mg of the reboxetine is administered twice a day to the human being for a first week.

10. The method of claim 9, wherein 4 mg of the reboxetine is administered to the human being in the morning and 4 mg of the reboxetine is administered to the human being in the afternoon for a second week.

11. The method of claim 1, wherein 6 mg of the reboxetine is administered to the human being in the morning and 4 mg of the reboxetine is administered to the human being in the afternoon for a first week.

12. The method of claim 11, wherein 6 mg of the reboxetine is administered to the human being in the morning and 4 mg of the reboxetine is administered to the human being in the afternoon for a second week.

13. The method of claim 1, wherein 5 mg of the reboxetine is administered to the human being in the morning and 5 mg of the reboxetine is administered to the human being in the afternoon for a first week.

14. The method of claim 13, wherein 5 mg of the reboxetine is administered to the human being in the morning and 5 mg of the reboxetine is administered to the human being in the afternoon for a second week.

* * * * *